(12) United States Patent
Oshlack et al.

(10) Patent No.: US 6,716,449 B2
(45) Date of Patent: Apr. 6, 2004

(54) CONTROLLED-RELEASE COMPOSITIONS CONTAINING OPIOID AGONIST AND ANTAGONIST

(75) Inventors: Benjamin Oshlack, New York, NY (US); Curtis Wright, Norwalk, CT (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/781,076

(22) Filed: Feb. 8, 2001

(65) Prior Publication Data

US 2002/0010127 A1 Jan. 24, 2002

Related U.S. Application Data

(60) Provisional application No. 60/181,358, filed on Feb. 8, 2000.

(51) Int. Cl.$^7$ ............................. A61F 13/00; A61K 9/70

(52) U.S. Cl. ................... 424/449; 604/304; 604/890.1

(58) Field of Search ............................. 424/422, 423, 424/424, 425, 426, 434, 443, 444, 445, 446, 447, 448, 449, 457, 458, 459, 460, 461, 462, 468, 467, 470, 471, 472, 473, 484, 485, 486, 487, 488, 489, 490, 491, 492, 493, 494, 495, 496, 497, 498, 499, 500, 501, 502; 604/289, 290, 304, 305, 306, 307, 308, 501, 890.1, 891.1, 892.1

(56) References Cited

U.S. PATENT DOCUMENTS

| | | | |
|---|---|---|---|
| 2,770,569 A | 11/1956 | Fromherz et al. | ............. 167/65 |
| 3,332,950 A | 7/1967 | Blumberg et al. | .......... 260/285 |
| 3,493,657 A | 2/1970 | Lewenstein et al. | ........ 424/260 |

(List continued on next page.)

FOREIGN PATENT DOCUMENTS

| | | | | |
|---|---|---|---|---|
| DE | 2222039 | 11/1972 | ........... | A61K/27/00 |
| DE | 4325465 | 2/1995 | ......... | A61K/31/485 |
| DE | 29719704 | 2/1997 | ......... | A61K/31/485 |
| DE | 19651551 | 6/1998 | ......... | A61K/31/485 |
| EP | 0205282 | 12/1986 | ............ | A61K/9/22 |
| EP | 0352361 | 1/1990 | ......... | A61K/31/485 |
| EP | 0647448 | 4/1995 | ......... | A61K/31/485 |
| EP | 0913152 | 6/1999 | ......... | A61K/31/485 |
| WO | 8303197 | 9/1983 | ............ | A61K/9/22 |
| WO | 9406426 | 3/1994 | ........... | A61K/31/46 |
| WO | 9503804 | 2/1995 | ......... | A61K/31/485 |
| WO | 9602251 | 2/1996 | ......... | A61K/31/485 |
| WO | 9733566 | 9/1997 | ............ | A61K/9/20 |
| WO | WO9825613 | 6/1998 | ......... | A61K/31/485 |
| WO | 9835679 | 8/1998 | ......... | A61K/31/485 |
| WO | 9932120 | 7/1999 | ......... | A61K/31/485 |
| WO | 00/01377 | * 1/2000 | | |
| WO | WO0038649 | 7/2000 | ............ | A61K/9/00 |

OTHER PUBLICATIONS

Sunshine, et al., "Analgesic Efficacy of Pentazocine Versus a Pentazocine–Naloxone Combination Following Oral Administration," Clin. J. Pain (1988), 4:35–40.
Wang et al., "Crossover and Parallel Study of Oral Analgesics," J. clin. Pharmacol (1981), 21:162–168.
Holmes et al., Anesth. Analg. (1993), 77:1166–73.
Miaskowski et al., Brain Research (1992), 596:41–45.
Weinhold et al., "Buprenorphine Alone and in Combination with Naltrexone in Non–Dependent Humans," Drug and Alcohol Dependence (1992), 30:263–274.
Cappel et al., Pharma. Bioch. & Behav. (1989), 34:425–427.
Vaccarino et al., Pain (1989), 36:103–109.
Gonzalez et al., "Naltrexone: A Review of its Pharmacodynamic and Pharmacokinetic Properties and Therapeutic Efficacy in the Management of Opioid Dependence," Drugs (1988), 35:192–213.
Chih–Cheng Chien, Neuroscience Letters 190 (1995), 137–139.
Crain et al., "Ultra–Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995), 92:10540–10544.
Hanson, Analgesic, Antipyretic and Anti–Inflammatory Drugs in Remington's Science and Practice of Pharmacy (1995), 2:1207.
Physician's Desk Reference 48$^{th}$ Ed. (1994) Montvale, NJ, 2120–2121.
Foss et al., J. Clin Pharmacol (1993), 33:747–751.
Mendelson J., et al., "Buprenorphine and Naloxone Interactions in Opiate–Dependent Volunteers," Clin. Phar. Ther. (1996), 60:105–114.
Walsh et al., "Effects of Naltrexone on Response to Intravenous Cocain, Hydromorphone and their Combination in Humans," (1996) (Abstract only).
Shen et al., "Ultra–Low Doses of Naltrexone or Etorphine Increase Morphine's Antinocieceptive Potencey and Attenuate Tolerance/Dependence in Mice," Brain Research (1997), 757:176–190.

(List continued on next page.)

Primary Examiner—Jeffrey E. Russel
(74) Attorney, Agent, or Firm—Davidson, Davidson & Kappel, LLC

(57) ABSTRACT

Controlled-release dosage forms containing an opioid agonist; an opioid antagonist; and a controlled release material release during a dosing interval an analgesic or subanalgesic amount of the opioid agonist along with an amount of the opioid antagonist effective to attenuate a side effect of the opioid agonist. The dosage form provides analgesia for at least about 8 hours when administered to human patients. In other embodiments, the dose of antagonist released during the dosing interval enhances the analgesic potency of the opioid agonist.

10 Claims, No Drawings

U.S. PATENT DOCUMENTS

| | | | |
|---|---|---|---|
| 3,676,557 A | 7/1972 | Lachman et al. | 424/260 |
| 3,773,955 A | 11/1973 | Pachter et al. | 424/260 |
| 3,879,555 A | 4/1975 | Pachter et al. | 424/260 |
| 3,966,940 A | 6/1976 | Pachter et al. | 424/260 |
| 4,176,186 A | 11/1979 | Goldberg | 424/260 |
| 4,401,672 A | 8/1983 | Portoghese | 424/260 |
| 4,451,470 A | 5/1984 | Ganti | 424/260 |
| 4,457,933 A | 7/1984 | Gordon et al. | 424/260 |
| 4,464,378 A | 8/1984 | Hussain et al. | 424/260 |
| 4,573,995 A | 3/1986 | Chen et al. | 604/896 |
| 4,582,835 A | 4/1986 | Lewis et al. | 514/282 |
| 4,608,376 A | 8/1986 | Pasternak | 514/282 |
| 4,661,492 A | 4/1987 | Lewis et al. | 514/282 |
| 4,719,215 A | 1/1988 | Goldberg | 514/282 |
| 4,730,048 A | 3/1988 | Portoghese | 546/45 |
| 4,760,069 A | 7/1988 | Rzeszotarski et al. | 514/282 |
| 4,769,372 A | 9/1988 | Kreek | 514/282 |
| 4,785,000 A | 11/1988 | Kreek et al. | 514/282 |
| 4,803,208 A | 2/1989 | Pasternak | 514/282 |
| 4,806,341 A | 2/1989 | Chien et al. | 424/448 |
| 4,806,543 A | 2/1989 | Choi | 514/464 |
| 4,806,558 A | 2/1989 | Wuest et al. | 514/381 |
| 4,861,598 A | 8/1989 | Oshlack et al. | 424/468 |
| 4,861,781 A | 8/1989 | Goldberg | 514/282 |
| 4,873,076 A | 10/1989 | Fishman et al. | 412/10 |
| 4,882,335 A | 11/1989 | Sinclair | 514/282 |
| 4,889,860 A | 12/1989 | Rzeszotarski et al. | 514/282 |
| 4,935,428 A | 6/1990 | Lewis | 514/282 |
| 5,075,341 A | 12/1991 | Mendelson et al. | 514/282 |
| 5,086,058 A | 2/1992 | Sinclair et al. | 514/282 |
| 5,096,715 A | 3/1992 | Sinclair | 424/449 |
| 5,102,887 A | 4/1992 | Goldberg | 514/282 |
| 5,149,538 A | 9/1992 | Granger et al. | 424/449 |
| 5,225,440 A | 7/1993 | London et al. | 514/535 |
| 5,236,714 A | 8/1993 | Lee et al. | 424/464 |
| 5,256,669 A | 10/1993 | Askanazi et al. | 514/282 |
| 5,273,760 A | 12/1993 | Oshlack et al. | 424/486 |
| 5,316,759 A | 5/1994 | Rose et al. | 424/10 |
| 5,317,022 A | 5/1994 | Borsodi et al. | 514/282 |
| 5,321,012 A | 6/1994 | Mayer et al. | 514/25 |
| 5,352,680 A | 10/1994 | Portoghese et al. | 514/279 |
| 5,352,683 A | 10/1994 | Mayer et al. | 514/289 |
| 5,356,900 A | 10/1994 | Bihari et al. | 514/282 |
| 5,376,662 A | 12/1994 | Ockert | 514/282 |
| 5,426,112 A | 6/1995 | Zagon et al. | 514/282 |
| 5,457,208 A | 10/1995 | Portoghese et al. | 546/35 |
| 5,472,943 A | 12/1995 | Crain et al. | 514/12 |
| 5,486,362 A | 1/1996 | Kitchell et al. | 424/426 |
| 5,502,058 A | 3/1996 | Mayer et al. | 514/289 |
| 5,512,578 A | 4/1996 | Crain et al. | 514/282 |
| 5,514,680 A | 5/1996 | Weber et al. | 514/249 |
| 5,534,492 A | 7/1996 | Aston et al. | 514/608 |
| 5,556,838 A | 9/1996 | Mayer et al. | 514/25 |
| 5,574,052 A | 11/1996 | Rose et al. | 514/343 |
| 5,578,725 A | 11/1996 | Portoghese et al. | 546/35 |
| 5,580,876 A | 12/1996 | Crain et al. | 514/282 |
| 5,585,348 A | 12/1996 | Crain et al. | 514/12 |
| 5,616,601 A | 4/1997 | Khanna et al. | 514/399 |
| 5,624,932 A | 4/1997 | Qin et al. | 514/282 |
| 5,633,259 A | 5/1997 | Qin et al. | 514/282 |
| 5,767,125 A | 6/1998 | Crain et al. | 514/282 |
| 5,858,017 A | 1/1999 | Demopulos et al. | 604/890.1 |
| 5,860,950 A | 1/1999 | Demopulos et al. | 604/49 |
| 5,866,164 A | 2/1999 | Kuczynski et al. | 424/472 |
| 5,880,132 A | 3/1999 | Hill | 514/282 |
| 5,942,241 A | 8/1999 | Chasin et al. | 424/426 |
| 5,968,547 A | 10/1999 | Reder et al. | 424/449 |
| 5,972,954 A | 10/1999 | Foss | 514/282 |
| 5,998,434 A | 12/1999 | Mitch et al. | 514/210.16 |
| 6,103,258 A * | 8/2000 | Simon | 424/449 |
| 6,228,863 B1 | 5/2001 | Palermo et al. | 514/282 |
| 6,277,384 B1 | 8/2001 | Kaiko et al. | 424/400 |

OTHER PUBLICATIONS

Yuan et al., Clinical Trials and Therapeutics (1997), 61:467–475.

Abstract, Cancer Chemother Pharmacol (1998); 42(4):287–91.

Yuan et al., Drug and Alcohol Dependence (1998); 52:161–165.

Gan et al., "Opioid–Sparing Effects of a Low–Dose Infusion of Naloxene in Patent–Administered Morphine Sulfate," Anesthesiology (1997), 87(5):1075–1080.

Press Release entitled "International Patent Application To Be Published on Abuse–Resistant Pain Reliever Being Developed by Purdue Pharma" Aug. 8, 2001.

Paronis, et al., Increased Analgesic Potency of Mu Agonists after Continuous Naloxone Infusion in Rats, J Pharm. Exper. Ther. 1991 259(2) p. 582–589.

Yoburn, et al., Supersensitivity to Opioid Analgesics Following Chronic Opioid Antagonist Treatment: Relationship to Receptor Selectivity, Pharmacol. Bio. Beh. 1995 51 (2) p 535–539.

Crain, et al., Acute thermal hyperalgesia elicited by low–dose morphine in normal mice is blocked by ultra–low–dose naltrexone, unmasking potent opioid analgesia, Brain Res. 2001 888 p 75–82.

Zhang, et al., Down–Regulation of $\mu$–Opioid Receptors in Rat and Monkey Dorsal Root Ganglion Neurons and Spinal Cord After Peripheral Axotomy, Neuroscience 1998 82, p 223–240.

Abdula, et al., Axotomy reduces the effect of analgesic opioids yet increases the effect of nociceptin on dorsal root ganglion neurons, J. Neuro Sci 1998 18;p 9685–9694.

Di Giannuario, et al., Orphanin FQ reduces morphine–induced dopamine release in the nucleus accumbens: a microdialysis study in rats, Neurosci. Lett. 1999 272, p 183–186.

Ciccocioppo, et al., Effect of nociceptin/orphanin FQ on the rewarding properties of morphine, Eur. J. Pharmacol. 2000 404, p 153–159.

Benfey, Function of Myocardial $\alpha$–Adrenoceptors: Life Sciences (1982) vol. 31 p 101–112.

Levine, et al., Potentiation of Pentazocine Analgesia by Low–dose Naloxone: J. Clin. Invest. (1988) vol. 82, p. 1574–1577.

Yoburn, et al., Opioid Antagonist–induced Receptor Upregulation: Effects of Concurrent Agonist Administration. (1994) (Publication Date): Brain Research Bulletin, vol. 33, p 237–240.

Bunzow, et al., Molecular cloning and tissue distribution of a putative member of the rat opioid receptor gene family that is not a $\mu$,$\delta$ κ or k opiod receptor type:FEBS Letters 347 (1994) p. 284–288.

Mollereau, et al., ORL1, a novel member of the opiod receptor family: Cloning, functional expression and localization: FEBS Letters 341 (1994) p. 33–38.

Wang, et al., cDNA cloning of an orphan opiate receptor gene family member and its splice variant: FEBS Letters 348 (1994) 75–79.

Suzuki et al., Morphine conditioned place reference after chronic treatment with naloxone in the rat Research Communications in Substances of Abuse. (1991) vol. 12, No. 3 p. 119–131.

* cited by examiner

CONTROLLED-RELEASE COMPOSITIONS CONTAINING OPIOID AGONIST AND ANTAGONIST

This application claims benefit of U.S. Provisional No. 60/181,358 filed Feb. 8, 2000 the disclosure of which is hereby incorporated by reference in its entirety.

BACKGROUND OF THE INVENTION

Opioids, also known as opioid agonists, are a group of drugs that exhibit opium or morphine-like properties. Opioid agonists are known in the literature and to those skilled in the art (Merck Manual, 16th Ed. (1992)). Because of their analgesic efficacy, opioid agonists have been used to provide pain relief to patients. Side effects are also associated with the use of opioid analgesics. For example, it has been reported that administration of opioid agonists such as morphine are associated with side effects, including nausea, vomiting, pruritis, urinary retention, and respiratory depression. Gan, et al. *Anesthesiology*, vol. 87, No. 5, 1075–1081 (1997). Chronic use of morphine has also been reported to increase physical dependence and increase tolerance of the drug, Shen et al., *Brain Res.*, Vol. 597, 74–83 (1992), and to induce constipation.

Attempts to reduce the side effects of opioid agonists, without affecting its analgesic efficacy, have also been reported. For example, Gan, et al. *Anesthesiology*, vol. 87, No. 5, 1075–1081 (1997) report that the administration of 0.25 $\mu$g.kg$^{-1}$.h$^{-1}$ or 1 $\mu$g.kg$^{-1}$.h$^{-1}$ naloxone (opioid antagonist) by infusion concomitantly with intravenous morphine, was effective in reducing certain potential side effects of morphine (e.g., the incidence of nausea, vomiting and prurities).

OBJECTS AND SUMMARY OF THE INVENTION

It is an object of the invention to promote patient compliance and thereby increase the efficacy of opioid agonist treatment in patients who are being treated with opioid agonist.

It is a further object of the invention to reduce the side effects associated with opioid agonist treatment.

It is also an object of the invention to provide agonist therapy in which the analgesically effective blood levels of the opioid agonist are maintained during an extended period of time, while also maintaining the pharmacologically effective blood levels of the antagonist for reducing the side effects associated with the opioid treatment.

It is also an object of the invention to enhance the analgesic potency of an opioid agonist in controlled release form and simultaneously attenuate development of physical dependence, tolerance and other undesirable side effects caused by the chronic administration of the opioid agonist.

It is also an object of the invention to provide agonist therapy in which analgesically effective blood levels of the opioid agonist are maintained over an extended period of time, while also selectively enhancing the analgesic potency of the opioid agonist. Preferably, the selective enhancement of analgesic potency of the opioid agonist occurs while simultaneously attenuating development of physical dependence, tolerance and other undesirable side effects caused by the chronic administration of the opioid agonist.

In view of the above-mentioned objects and others, the invention is directed to a controlled release oral dosage form comprising opioid agonist and opioid antagonist, wherein the dosage form releases the opioid agonist and the antagonist in a controlled-release manner.

The invention is further directed to a controlled-release dosage form comprising an opioid agonist and the opioid antagonist, wherein the opioid agonist or the opioid antagonist, before it is combined with the other, is treated to modify its release rate, such that when combined into the controlled-release dosage form, the opioid agonist and the antagonist are released from the dosage form at appropriately similar times.

The invention is further directed to a controlled-release dosage form comprising opioid agonist and opioid antagonist, wherein the opioid agonist is present in an amount that is analgesically effective when administered to a human, and wherein the opioid antagonist is present in an amount which does not cause a reduction in the level of analgesia provided by the dosage form to a non-therapeutic level. In certain embodiments, the opioid antagonist is also present in an amount that is effective in reducing opioid-related side effects.

In certain embodiments of the present invention, the controlled release dosage form comprises a transdermal delivery system, an oral mucosal delivery system, a composition for intranasal administration, an injectable composition, and a solid oral composition.

In certain preferred embodiments, the present invention comprises a controlled release dosage form that delivers an opioid agonist and an opioid antagonist over an extended period of time. In these oral embodiments, the dosage form includes an amount of an opioid agonist, preferably a bimodally-acting opioid agonist, and an amount of an opioid antagonist, and upon administration the dosage form delivers an analgesic or sub-analgesic amount of the opioid agonist over the dosing interval, along with an amount of the opioid antagonist effective to enhance the analgesic potency of the opioid agonist and attenuate the anti-analgesia, hyperalgesia, hyperexcitability, physical dependence and/or tolerance effects of the opioid agonist.

Certain embodiments of the invention are directed to controlled-release dosage forms comprising an opioid agonist and the opioid antagonist, wherein the opioid agonist or the opioid antagonist, before it is combined with the other, is treated to modify its release rate, such that when combined into the controlled-release dosage form, the opioid agonist and the antagonist are released from the dosage form at appropriately similar times.

The present invention is also directed to the use of the above-mentioned controlled release formulations for maintenance treatment of previously detoxified opiate addicts.

In certain preferred embodiments, the opioid agonist is selected from the group consisting of hydromorphone, oxycodone, hydrocodone, morphine, pharmaceutically acceptable salts thereof and mixtures thereof.

In certain preferred embodiments, the opioid agonist is a bimodally-acting opioid agonist selected from, e.g., morphine, codeine, fentanyl analogs, pentazocine, buprenorphine, methadone, enkephalins, dynorphins, endorphins, and similarly acting opioid alkaloids and opioid peptides.

In certain preferred embodiments, the opioid antagonist is selected from the group consisting of naltrexone, naloxone, nalmefene, pharmaceutically acceptable salt thereof and mixtures thereof.

DETAILED DESCRIPTION OF THE INVENTION

The present invention is directed to controlled-release dosage forms comprising an opioid agonist and an opioid antagonist, the dosage form providing controlled-release of the opioid agonist and controlled-release of the opioid antagonist. In preferred embodiments, the release rate of the agonist and the antagonist from the dosage form are controlled to maintain an analgesically effective amount of the agonist in the blood throughout the dosing period and to maintain the concentration of the opioid antagonist throughout the dosing period sufficient for decreasing the side effects associated with the opioid agonist but not sufficient to negate the analgesic efficacy of the agonist. In preferred embodiments, the invention is directed to controlled release solid dosage forms that release an opioid agonist and an opioid antagonist over an extended period of time. In these oral embodiments, the dosage form includes an amount of an opioid agonist, preferably a biomodally-acting opioid agonist, and an amount of an opioid antagonist, and upon oral administration the dosage form releases an analgesic or sub-analgesic amount of the opioid agonist over the dosing interval, along with an amount of the opioid antagonist effective to enhance the analgesic potency of the opioid agonist and attenuate the anti-analgesia, hyperalgesia, hyperexcitability, physical dependence and/or tolerance effects of the opioid agonist.

The present invention is further directed to a controlled-release solid oral dosage form comprising an opioid agonist and an opioid antagonist, the dosage form providing controlled-release of the opioid agonist and controlled-release of the opioid antagonist, the dosage form, when administered to patients, providing analgesia together with reduction of side effects associated with the opioid agonist. It is preferred that such dosage form releases the opioid agonist and the antagonist at substantially proportionate rates. Preferably, the release rates of the opioid agonist and antagonist are approximately proportionate over time, more preferably over a dosing period.

In certain embodiments, the controlled-release composition of the present invention provides reduction of opioid associated side effects, e.g., nausea, vomiting, pruritis, urinary retention, respiratory depression, constipation, physical dependence, tolerance, hyperexcitability, and hyperalgeia.

U.S. Pat. Nos. 5,512,578; 5,472,943; 5,580,876; and 5,767,125, (Crain et al.), each of which are hereby incorporated by reference in their entireties, describe combinations of opioid antagonists with morphine or other bimodally acting opioid agonists. The combinations described therein are said to enhance the analgesic effects of the bimodal opioid agonist, while at the same time attenuating the physical dependence, tolerance, hyperexcitability, hyperalgeia, and other undesirable (excitatory) side effects associated with chronic use of bi-modally acting opioid agonists. However, these patents do not contemplate providing a mechanism or manner of preparation of the combination dosage form in which the agonist and the antagonist are each released from the dosage form in a controlled-release manner, allowing the agonist and antagonist to be absorbed by (or delivered to) the patient, such that the requisite analgesia together with reduction of opioid agonist related side effects and/or increased opioid potency may be provided throughout a prolonged dosing period. The above-cited documents also do not provide controlled-release formulations for maintaining the analgesically effective blood levels of agonist during an extended period of time, while at the same time maintaining the pharmacologically effective blood levels of the antagonist for reducing the side effects associated with the opioid treatment. Such controlled-release compositions would be desirable, e.g., because they would allow for the limitation of peak concentrations and increase patient compliance because the drug is taken less frequently.

The term "controlled-release dosage form," refers to a dosage form which provides a longer period of pharmacological response after the administration of the agonist and the antagonist than is ordinarily provided after the administration of the rapid release dosage form. In certain preferred embodiments of the invention, the controlled-release dosage form releases the opioid agonist and the opioid agonist from the dosage form at such a rate that blood (e.g., plasma) concentration (levels) are maintained within the analgesically effective range (above the minimum effective analgesic concentration or "MEAC") over a dosing period. In certain embodiments of the invention, the opioid antagonist is released from the controlled-release dosage form at such a rate that blood (e.g., plasma) concentration of the antagonist are maintained within the pharmacologically effective range for reducing the opioid agonist associated side effects over a dosing period. In other preferred embodiments, the opioid antagonist is delivered from the controlled-release dosage form at such a rate that the controlled release formulations provide the benefits set forth in the above-mentioned Crain, et al. patents, namely, enhancement of the analgesic potency of the opioid agonist while simultaneously attenuating anti-analgesia, hyperalgesia, hyperexcitability, physical dependence and/or tolerance effects of the opioid agonist. One skilled in the art will understand that due to the enhancement of analgesia caused by the particular combinations of opioid agonist/opioid antagonist encompassed by the present invention, the analgesic efficacy may be greater than that reflected by blood plasma levels of the opioid agonist. For purposes of the present invention, the controlled release obtained via in-vitro dissolution testing of the formulation (i.e., measuring the release of the opioid agonist and the opioid antagonist) may serve as a surrogate measure of the dosing interval for the controlled release dosage form in-vivo, particularly in the case of oral formulations. Such in-vitro testing may be undertaken utilizing the USP Paddle Method of U.S. Pharmacopeia XXII (1990) at 100 rpm at 900 ml aqueous buffer (pH between 1.6 and 7.2) at 37° C. The analytical method may be, e.g., high performance liquid chromatography.

In preferred embodiments, the controlled-release dosage form of the present invention is administrable (i.e., provides the requisite effects stated above) at least every 8 hours. In certain preferred embodiments, the controlled release dosage form is administrable twice daily (every 12 hours), or once-a-day (every 24 hours). In embodiments where the controlled release dosage form is a transdermal delivery system, the transdermal delivery system preferably provides the requisite effect for at least about 3 days. In certain preferred embodiments, the transdermal delivery system may be worn on the skin of a human patient for at least about 5 days, and preferably about 7 days, while provided attenuation of the anti-analgesia, hyperalgesia, hyperexcitability, physical dependence and/or tolerance effects of the opioid agonist. Preferably, the opioid antagonist simultaneously provides enhancement of the analgesic potency of the opioid agonist.

In the present invention, a very low dose of an opioid antagonist is combined with a dose of an opioid agonist (analgesic) so as to enhance the degree of analgesia an attenuate undesired side effects. The dosage form is prepared in a manner which causes the opioid agonist and the opioid antagonist to be delivered when the dosage form is administered, e.g., to a human patient.

The rate of delivery of the opioid agonist will be such that substantially the entire dose of opioid agonist contained in the dosage form is delivered from the dosage form after administration, in those embodiments in which the controlled release dosage form is an oral mucosal delivery system, a composition for intranasal administration, an injectable composition, and a solid oral composition. The rate of delivery of the opioid antagonist will be such that an effective amount of the opioid antagonist is delivered to attenuate the anti-analgesia, hyperalgesia, hyperexcitability, physical dependence and/or tolerance effects of the opioid agonist during the intended dosing interval. Preferably, rate of delivery of the opioid antagonist will be such that an effective amount of the opioid antagonist is delivered to enhance the analgesic potency of the opioid analgesic during the dosing interval of the controlled release dosage form. It is not necessary that substantially all of the opioid antagonist be delivered from the controlled release dosage form to meet these goals.

When the controlled release dosage form comprises a transdermal delivery system, the rate of delivery of the opioid agonist will be such that a sufficient mean relative release rate (or flux rate) of the opioid agonist contained in the dosage form is delivered from the transdermal dosage form upon administration. The rate of delivery of the opioid antagonist will be such that an effective amount of the opioid antagonist is delivered to attenuate the anti-analgesia, hyperalgesia, hyperexcitability, physical dependence and/or tolerance effects of the opioid agonist during the intended dosing interval. Preferably, rate of delivery of the opioid antagonist will be such that an effective amount of the opioid antagonist is delivered to enhance the analgesic potency of the opioid analgesic during the dosing interval of the controlled release dosage form. It is not necessary that substantially all of the opioid antagonist be delivered from the controlled release dosage form to meet these goals.

In accordance with the present invention, the dose of opioid antagonist which is delivered from the dosage form during the dosing interval is preferably from about 100 to about 1000 times less than the dose of the opioid agonist (preferably, bimodally-acting opioid agonist) delivered from the dosage form. As described in the Crain, et al. patents mentioned above, excitatory opioid receptor antagonists bind to and inactivate excitatory opioid receptors on neurons in the nociceptive pathways. The excitatory opioid receptor antagonists of the invention are preferably seleted from the group consisting of naloxone, naltrexone, diprenorphine, etorphine and dihydroetorphine. Naltrexone and naloxone are especially preferred in certain embodiments of the invention.

The controlled release dosage forms of the present invention preferably deliver the opioid antagonist (e.g., excitatory opioid receptor antagonists) at such a level that the opioid antagonist has selective antagonist action at excitatory, but not inhibitory, opioid receptors. In addition, since the antagonists preferably enhance the analgesic potency of the agonists, the agonists become effective when administered at reduced doses which would otherwise be subanalgesic. It may be possible to achieve an analgesic effect with 10–100 times lower doses of the (bimodally acting) opioid agonists with the excitatory opioid receptor antagonists of the invention than when the opioid agonist is administered alone. This is because the excitatory opioid receptor antagonists may enhance the analgesic effects of the opioid agonists by attenuating the anti-analgesic excitatory side effects of the opioid agonists. Therefore, in certain preferred embodiments of the invention, the opioid agonist is included in the dosage form and is delivered in an amount which is less than that which has been typically administered for analgesia. In certain embodiments of the invention, the opioid antagonist is delivered such that the amount of opioid agonist included in the dosage form is, e.g., about 10 to about 100 times less than the amount of that opioid agonist typically dosed over the dosing interval.

Certain embodiments of the invention are directed to controlled-release dosage forms comprising an opioid agonist and the opioid antagonist wherein the opioid agonist or the opioid antagonist, before it is combined with the other, is treated to modify its release rate, such that when combined into the controlled-release dosage form, the opioid agonist and the antagonist are released from the dosage form at appropriately similar times. For example, one of the drugs may be pretreated, e.g., with a controlled release material, to modify its release rate such that when combined into a unitary dosage form with the other drug, the release rates of the two drugs will be substantially similar.

It may also be possible to obtain a similar release rate for both the opioid agonist and opioid antagonist, in situations where the drugs chosen would provide different release rates from the controlled release dosage form because, e.g., they have differing solubilities, by choosing a salt of one of the drugs which provides a closer match in solubilities. Additionally (or alternatively), the particular choice of opioid antagonist can be matched as closely as possible with respect to the solubility of the opioid analgesic.

Alternatively, in certain embodiments of the present invention it is not necessary to adjust release rates, etc. as set forth above due to the choice of agonist and/or antagonist which has, for example, a long half-life.

In addition, the excitatory opioid receptor antagonists can be administered in the controlled release formulations of the invention along with sub-analgesic doses of opioid receptor agonists for long-term maintenance treatment of previously detoxified opiate, cocaine and alcohol addicts to prevent protracted physical dependence.

Opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphine, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the like.

In certain preferred embodiments, the bimodally-acting opioid agonist is selected from the group consisting of morphine, codeine, fentanyl analogs, pentazocine, methadone, buprenorphine, enkephalins, dynorphins, endorphins and similarly acting opioid alkaloids and opioid peptides.

In certain preferred embodiments, the opioid agonist is selected from the group consisting of hydrocodone, morphine, hydromorphone, oxycodone, codeine, levorphanol, meperidine, methadone, or salts thereof or mixtures thereof. In certain preferred embodiments, the opioid agonist is oxycodone or hydrocodone. Equianalgesic doses of these opioids, in comparison to a 15 mg dose of hydrocodone, are set forth in Table 1 below:

TABLE 1

Equianalgesic Doses of Opioids

| Opioid | Calculated Dose (mg) |
|---|---|
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

In certain embodiments of the invention, the opioid agonist is a bimodally acting opioid agonist. "Bimodally acting opioid agonists" are opioid agonist that bind to and activate both inhibitory and excitatory opioid receptors on nociceptive neurons which mediate pain. Activation of the inhibitory receptors results in opioid analgesia, whereas the activation of the excitatory receptors results in undesirable side effects, including the development of physical dependence and tolerance to the opioid agonist, anti-analgesic actions, hyperexcitability and hyperalgeia. Examples of bimodally acting opioid agonists include morphine, codeine, fenfenyl analogs, pentazocine, methadone, buprenorphine, enkephalins, dynorphias, endorphins and similarly acting opioid alkaloids and opioid peptides.

The excitatory opioid receptor antagonists of the invention are preferably selected from the group consisting of naloxone, naltrexone, diprenorphine, etorphine, dihydroetorphine, pharmaceutically acceptable salts thereof and mixtures thereof. Other opioid antagonists include nalinefene, cyclazacine, levallorphan, pharmaceutically acceptable salts thereof and mixtures thereof. In certain referred embodiments, the opioid antagonist is naloxone or naltrexone.

For purposes of the present invention, the term "opioid agonist" is interchangeable with the term "opioid" or "opioid analgesic" and shall include the base of the opioid, mixed agonist-antagonists, partial agonists, pharmaceutically acceptable salts thereof, stereoisomers thereof, ethers and esters thereof, and mixtures thereof.

For purposes of the present invention, the term "opioid antagonist" shall include the base, pharmaceutically acceptable salts thereof, stereoisomers thereof, ethers and esters thereof, and mixtures thereof.

The invention disclosed herein is meant to encompass all pharmaceutically acceptable salts thereof of the disclosed opioid agonists and antagonists. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

Some of the opioid agonists and antagonists disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The present invention is further directed to a method of decreasing the potential for abuse of an opioid agonist in an oral dosage form. The method comprises providing the opioid agonist in an oral dosage form as described herein.

The controlled-release compositions of the present invention includes, but is not limited to, a transdermal delivery system, an oral mucosal delivery system, a composition for intranasal administration, an injectable composition, and a solid oral composition.

Transdermal Delivery System

The controlled release formulations of the present invention may be formulated as a transdermal delivery system, such as transdermal patches. In certain embodiments of the present invention, a transdermal patch comprises an opioid agonist and an opioid antagonist contained in a reservoir or a matrix, and an adhesive which allows the transdermal device to adhere to the skin, allowing the passage of the active agent from the transdermal device through the skin of the patient. Once the agonist/antagonist has penetrated the skin layer, the drugs are absorbed into the blood stream where they exert desired pharmaceutical effects. The transdermal patch releases both the opioid agonist and the opioid antagonist in a controlled-release manner, such that the blood levels of the opioid agonist is maintained at an analgesically effective level through out the dosing period, and the blood levels of the antagonist is maintained at a concentration that is sufficient to reduce side effects associated with the opioid agonist but not sufficient to negate the analgesic effectiveness of the opioid. Preferably, the amount of antagonist delivered from the transdermal delivery system is effective to enhance the analgesic potency of the opioid agonist delivered from the dosage form.

Transdermal delivery system providing a controlled-release of an opioid agonist is known. For example, Duragesic® patch (commercially available from Janssen Pharmaceutical) contains an opioid agonist (fentanyl) and is said to provide adequate analgesia for up to 48 to 72 hours (2 to 3 days).

Transdermal delivery systems containing buprenorphine (an opioid agonist), for providing prolonged analgesia, are also described. Although other types of opioid analgesic transdermal formulations have been reported in the literature (such as fentanyl, discussed above), buprenorphine transdermal delivery systems are of particular interest because buprenorphine is a potent, partial agonist opioid analgesic with desirable therapeutic properties. For example, buprenorphine is 50 to 100 times more potent than morphine, but has a much safer therapeutic index than morphine (see Wallenstein S L, et al., *Crossover Trials in Clinical Analgesic Assays: Studies of Buprenorphine and Morphine,* Pharmacotherapy, G(5): 225–235, 1986 hereby incorporated by reference).

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al.), all of which are hereby incorporated by reference.

The transdermal delivery system used in the present invention may also be prepared in accordance with U.S. Pat. No. 5,069,909 (Sharma et al.), hereby incorporated by reference. This patent describes a laminated composite for administering buprenorphine transdermally to treat pain. The transdermal delivery system used in the present invention may also be prepared in accordance with U.S. Pat. No. 4,806,341 (Chien et al.), hereby incorporated by reference. This patent describes a transdermal morphinan narcotic analgesic or antagonist (including buprenorphine) pharmaceutical polymer matrix dosage unit having a backing layer which is substantially impervious to the buprenorphine, and a polymer matrix disc layer which is adhered to the backing layer and which has microdispersed therein effective dosage amounts of the buprenorphine.

The transdermal delivery system used in the present invention may also be that described in U.S. Pat. No. 5,026,556 (Drust et al.), hereby incorporated by reference. Therein, compositions for the transdermal delivery of buprenorphine comprise buprenorphine in a carrier of a polar solvent material selected from the group consisting of $C_3$–$C_4$ diols, $C_3$–$C_6$ triols, and mixtures thereof, and a polar lipid material selected from the group consisting of fatty alcohol esters, fatty acid esters, and mixtures thereof; wherein the polar solvent material and the lipid material are present in a weight ratio of solvent material:lipid material of from 60:40 to about 99:1. The transdermal delivery system used in the present invention may also be that described in U.S. Pat. No. 4,588,580 (Gale, et. al.), hereby incorporated by reference. That system comprises a reservoir for the drug having a skin proximal, material releasing surface area in the range of about 5–100 cm² and containing between 0.1 and 50% by weight of a skin permeable form of the buprenorphine. The reservoir contains an aqueous gel comprising up to about 47–95% ethanol, 1–10% gelling agent, 0.1–10% buprenorphine, and release rate controlling means disposed in the flow path of the drug to the skin which limits the flux of the buprenorphine from the system through the skin.

The present invention is contemplated to encompass all transdermal formulations, e.g., the technologies described above, with the inclusion of an opioid antagonist, such that the opioid antagonist is released in a controlled-release manner along with the opioid agonist.

The transdermal delivery systems of the invention preferably deliver an analgesic or sub-analgesic amount of the opioid agonist together with an amount of the opioid antagonist effective to attenuate the anti-analgesia, hyperalgesia, hyperexcitability, physical dependence and/or tolerance effects of the opioid agonist. Preferably, the amount of opioid antagonist delivered simultaneously enhances the analgesic potency of the opioid agonist delivered from the transdermal delivery system.

The transdermal delivery systems may deliver the opioid agonist and/or the opioid antagonist in accordance with first order pharmacokinetics, zero order pharmacokinetics, or both first and zero order pharmacokinetics during the dosing interval. The term "first order" pharmacokinetics is defined as plasma concentrations which increase over a specified time period. The term "zero order" pharmacokinetics contemplates an amount of drug released from a buprenorphine formulation which substantially maintains plasma concentrations at a relatively constant level. For purposes of the present invention, a relatively constant plasma concentration is defined as a concentration which does not decrease more than about 30% over a 48 hour time period.

The term "delivers" when used with respect to transdermal delivery devices means that the transdermal delivery device provides a mean relative release rate or flux of the drug out of the device and through the skin of the patient. The term "mean relative release rate" is determined from the amount of drug released per unit time from the transdermal delivery device through the skin and into the bloodstream of a human patient. Mean relative release rate may be expressed, e.g, as g drug/cm²/hr. For example, a transdermal delivery device that releases 1.2 mg of buprenorphine over a time period of 72 hours is considered to have a relative release rate of 16.67 g/hr. For purposes of the invention, it is understood that relative release rates may change between any particular time points within a particular dosing interval, and the term therefore only reflects the overall release rate during the particular dosing interval. For purposes of the present invention, relative release rate should be considered synonomous with the term "flux rate".

For example, delivery of buprenorphine transdermally to human patients has previously been reported, e.g., in U.S. Pat. No. 5,968,547, hereby incorporated by reference, such that mean relative release rates are achieved as follows: a mean relative release rate of from about 3 g/hr to about 86 g/hr from initiation of the dosing interval until about 72 hours thereafter; and a mean relative release rate of about 0.3 g/hr to about 9 g/hr from about 72 hours after the initiation of the dosing interval until at least about 120 hours after the initiation of the dosing interval.

In certain embodiments of transdermal dosage form is a transdermal patch comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of said opioid agonist and opioid antagonist and 0.1 to 30% of a solvent for the opioid agonist and opioid antagonist.

The controlled release dosage form can also comprise a transdermal plaster comprising:

(1) a film layer which comprises a polyester film of 0.5 to 4.9 μm thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which (a) the average particle size is 0.001 to 3.0. μm, and (b) the average particle size is substantially not more than 1.5 times the thickness of said polyester film; and (2) an adhesive layer (a) which is composed of an adhesive containing said opioid agonist and opioid antagonist and further wherein said adhesive layer (a) is laminated on said film layer over the surface in a 2 to 60 μm thickness.

The controlled release dosage can be a transdermal patch comprising a laminated composite for administering said opioid agonist and opioid antagonist to an individual transdermally comprising: (a) a polymer backing layer that is substantially impermeable to said opioid agonist and opioid antagonist; and (b) a reservoir layer comprising a water-base acrylate pressure-sensitive adhesive, 1 to 12% by weight opioid agonist and opioid antagonist and 2 to 25% by weight of a permeation enhancer comprising propylene glycol monolaurate in combination with capric acid or oleic acid, wherein the skin contact area of the composite is 10 to 100 cm.sup. 2 and the rate of administration from the composite is about 1 to about 100 μg/hr.

The controlled release dosage form can be a transdermal patch comprising: (a) a backing layer which is substantially impervious to said opioid agonist and opioid antagonist; and (b) a polymer matrix layer which is adhered to said backing layer and which has dispersed therein said opioid agonist and opioid antagonist, said polymer being bioacceptable and permitting said opioid agonist and opioid antagonist to be transmitted for transdermal absorption, said opioid agonist and opioid antagonist being stable in said polymer matrix.

The controlled release dosage form can be a transdermal patch comprising (a) a polar solvent material selected from the group consisting of $C_3$–$C_4$ diols, $C_3$–$C_6$ triols, and mixtures thereof; and (b) a polar lipid material selected from the group consisting of fatty alcohol esters, fatty acid esters, and mixtures thereof; wherein said polar solvent material and said polar lipid material are present in a weight ratio of solvent material:lipid material of from about 60:40 to about 99:1.

Oral Mucosal Delivery System

In certain embodiments of the present invention, the controlled release opioid agonist/antagonist formulation may be prepared as a controlled-release oral mucosal delivery system. Such a system is described by McQuinn, R. L. et al., "Sustained Oral Mucosal Delivery in Human Volunteers *J. Controlled Release;* (34) 1995 (243–250). Therein, oral mucosal patches were prepared by homogeneously mixing buprenorphine free base (8%), Carbopol 934 (52%), polyisobutylene (35%) and polyisoprene (5%, w/w) via a two-roll mill and then compressing the mixture to the appropriate thickness. A membrane backing (ethylcellulose) was applied to one side of the compressed material and then circular disks (0.5 cm$^2$) were punched from the material. The backing was included in order to retard drug release from one side of the disk and to prohibit adhesion to opposing side tissues. Each soft, flexible disk was approximately 0.6 mm thick and contained 2.9 mg buprenorphine. These patches were worn by the subjects for 12 hours. Gum and lip application was tested, although adhesion at the gum site was considered superior. After the initial appearance of serum buprenorphine ($\geq$25 pg/ml), levels generally increased relatively rapidly and persisted until the patch was removed. After the patch was removed, buprenorphine levels fell promptly and were at a relatively low (but measureable) level by 24 hours post-dose. It was estimated that 0.42±0.18 mg were delivered via the gum treatment. From this discussion, it is apparent that an oral mucosal patch can be prepared which will provide plasma concentrations considered desirable according to the present invention.

The present invention is contemplated to encompass all oral mucosal delivery systems, e.g., the technologies described above, with the inclusion of an opioid antagonist, such that the opioid antagonist is released in a controlled-release manner along with the opioid agonist.

For example, the oral mucosal delivery device can comprise a compressed mixture comprising a polymer with a cellulose backing. The polymer can be selected from the group consisting of Carbopol 934, polyisobutylene, polyisoprene and mixtures thereof and said cellulose can be an alkylcellulose, e.g., ethylcellulose.

Suppositories

The controlled release formulations of the present invention may be formulated as a pharmaceutical suppository for rectal administration comprising an opioid agonist and an opioid antagonist in a controlled release matrix, and a suppository vehicle (base). Preparation of controlled release suppository formulations is described in, e.g., U.S. Pat. No. 5,215,758, hereby incorporated by reference in its entirety.

Prior to absorption, the drug must be in solution. In the case of suppositories, solution must be preceded by dissolution of the base, or the melting of the base and subsequent partition of the drug from the base into the rectal fluid. The absorption of the drug into the body may be altered by the suppository base. Thus, the particular base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factor affecting the absorption of drugs from suppositories administered rectally include suppository vehicle, absorption site pH, drug pKa, degree of ionization, and lipid solubility.

The suppository base chosen should be compatible with the opioid agonist/antagonist to be incorporated into the composition. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural. fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12–18 carbon atom chain sold under the trade name Novata TM (types AB, AB, B, BC, BD, BBC, E, BCF, C, D and 299), manufactured by Henkel, and Witepsol TM (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of alginate and drug used. Generally, the amount of suppository base is from about 20 percent to about 90 percent by weight of the total weight of the suppository. Preferably, the amount of base in the suppository is from about 65 percent to about 80 percent, by weight of the total weight of the suppository.

In certain embodiments, the controlled-release matrix comprises a pharmaceutically acceptable sodium alginate and a pharmaceutically acceptable calcium salt, the calcium salt being in an amount sufficient to cross-link with the sodium alginate and thereby provide controlled-release of the opioid agonist and the antagonist from the matrix when the suppository base melts subsequent to administration.

The present invention is contemplated to encompass all suppository systems, e.g., the technologies described above, with the inclusion of an opioid antagonist, such that the opioid antagonist is released in a controlled-release manner along with the opioid agonist.

For example, the suppository can comprise a controlled release matrix comprising a pharmaceutically acceptable sodium alginate and a pharmaceutically acceptable calcium, and a suitable vehicle which melts or dissolves in rectal fluids, said calcium salt being in an amount sufficient to cross-link with the sodium alginate and thereby provide a controlled release of said therapeutically active agent from said matrix when said vehicle melts or dissolves. The calcium salt can be selected from the group consisting of calcium phosphate, dicalcium phosphate, calcium chloride, calcium carbonate, calcium acetate, calcium gluconate, and mixtures thereof.

Compositions for Intranasal Administration

The controlled release formulation of the present invention includes compositions for nasal administration. Controlled release dosage forms containing an opioid agonist is described in European Patent No. EP 205282 and PCT Application No. WO 8203768 (both providing controlled release of morphine), and also in U.S. Pat. No. 5,629,011 (morphine-6-glucuronide and morphine-6-sulfate, both being metabolites of morphine). Each of these documents are incorporated herein by reference in their entireties. The present invention is contemplated to encompass all such nasal formulations as described above, with the inclusion of an opioid antagonist, such that the opioid antagonist is released in a controlled-release manner.

In certain embodiments, the nasal composition comprises an opioid agonist and the opioid antagonist in bioadhesive microspheres. Preferably the microspheres are prepared from a bio-compatible material that will gel in contact with the mucosal surface. Substantially uniform solid microspheres are preferred. Starch microspheres (crosslinked if necessary) are a preferred material. Other materials that can be used to form microspheres include starch derivatives, modified starches such as amylodextrin, gelatin, albumin, collagen, dextran and dextran derivatives, polyvinyl alcohol, polylactide-co-glycolide, hyaluronic acid and derivatives thereof such as benzyl and ethyl esters, gellan gum and derivatives thereof such as benzyl and ethyl esters and pectin and derivatives thereof such as benzyl and ethyl esters. By the term "derivatives" we particularly mean esters and ethers of the parent compound that can be unfunctionalised or functionalised to contain, for example, ionic groupings.

Suitable starch derivatives include hydroxyethyl starch, hydroxypropyl starch, carboxymethyl starch, cationic starch, acetylated starch, phosphorylated starch, succinate derivatives of starch and grafted starches. Such starch derivatives are well known and described in the art (for example Modified Starches: Properties and Uses, O. B. Wurzburg, CRC Press Boca Raton (1986)).

Suitable dextran derivatives include, diethylaminoethyl-dextran (DEAE-dextran), dextran sulphate, dextran methylbenzylamide sulphonates, dextran methyl-benzylamide carboxylates, carboxymethyl dextran, diphosphonate dextran, dextran hydrazide, palmitoyldextran and dextran phosphate.

Preparation of these microspheres is well described in the pharmaceutical literature (see for example Davis et al., (Eds), "Microspheres and Drug Therapy", Elsevier Biomedical Press, 1984, which is incorporated herein by reference). Emulsion and phase separation methods are both suitable. For example, albumin microspheres may be made using the water-in-oil emulsification method where a dispersion of albumin is produced in a suitable oil by homogenization techniques or stirring techniques, with the addition if necessary of small amounts of an appropriate surface active agent. The size of the microspheres is largely dictated by the speed of stirring or homogenization conditions. The agitation can be provided by a simple laboratory stirrer or by more sophisticated devices such as a microfluidizer or homogenizer. Emulsification techniques are also used to produce starch microspheres as described in GB 1 518 121 and EP 223 303 as well as for the preparation of microspheres of gelatin. Proteinaceous microspheres may also be prepared by coacervation methods such as simple or complex coacervation or by phase separation techniques using an appropriate solvent or electrolyte solution. Full details of the methods of preparing these systems can be obtained from standard text books (see for example Florence and Attwood, Physicochemical Principles of Pharmacy 2nd Ed., MacMillan Press, 1988, Chapter 8).

The controlled-release nasal composition according to the invention can be administered by any appropriate method according to their form. A composition comprising microspheres or a powder can be administered using a nasal insufflator device. Examples of these are already employed for commercial powder systems intended for nasal application (e.g. Fisons Lomudal System).

The insufflator produces a finely divided cloud of the dry powder or microspheres. The insufflator is preferably provided with means to ensure administration of a substantially fixed amount of the composition. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator preferably has means to break open the capsule or other device.

A composition comprising a solution or dispersion in an aqueous medium can be administered as a spray using an appropriate device such as a metered dose aerosol valve or a metered dose pump. A gas or liquid propellant can be used.

Details of other devices can be found in the pharmaceutical literature (see for example Bell, A. Intranasal Delivery Devices, in Drug Delivery Devices Fundamentals and Applications, Tyle P. (ed), Dekker, New York, 1988), Remington's Pharmaceutical Sciences, Mack Publishing Co., 1975.

The present invention is contemplated to encompass all nasal formulations, e.g., the technologies described above, with the inclusion of an opioid antagonist, such that the opioid antagonist is released in a controlled-release manner along with the opioid agonist.

For example, the intranasal formulation can comprise an effective amount of an absorption promoting agent to allow nasal absorption of the agents after nasal administration of the composition. The absorption promoting agent can be selected from the group consisting of a cationic polymer, a surface active agent, a chelating agent, a mucolytic agent, a cyclodextrin, and combinations thereof.

Injectable Formulations

The controlled-release injectable compositions containing an opioid antagonist is described in, e.g., U.S. Pat. No. 5,942,241 to Chasin et al, which is incorporated herein by reference in its entirety. The present invention is contemplated to encompass all such injectable formulations, with the inclusion of an opioid antagonist, such that the opioid antagonist is also released in a controlled-release manner along with the opioid agonist.

In certain embodiments, the controlled-release injectable composition comprise an opioid agonist and antagonist in controlled-release microparticles, e.g., microspheres or microcapsules. The slow release of the drugs is brought about through controlled diffusion out of the matrix and/or selective breakdown of the coating of the preparation or selective breakdown of a polymer matrix.

In certain embodiments, the slow release formulation is prepared as microspheres in a size distribution range suitable for local infiltration or injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. In addition, other particle shapes, such as, for example, cylindrical shapes, can also modify release rates by virtue of the increased ratio of surface area to mass inherent to such alternative geometrical shapes, relative to a spherical shape. The diameter of injectable microspheres are in a size range from, for example, from about 5 microns to about 200 microns in diameter. In a more preferred embodiment, the microspheres range in diameter from about 20 to about 120 microns.

A wide variety of biodegradable materials may be utilized to provide the controlled release injectable dosage forms. Any pharmaceutically acceptable biodegradable polymers known to those skilled in the art may be utilized. It is preferred that the biodegradable controlled release material degrade in vivo over a period of less than about two years, with at least 50% of the controlled release material degrading within about one year, and more preferably six months or less. More preferably, the controlled release material will degrade significantly within one to three months, with at least 50% of the material degrading into non-toxic residues which are removed by the body, and 100% of the drug being released within a time period from about two weeks to about two months. The controlled release material should preferably degrade by hydrolysis, and most preferably by surface erosion, rather than by bulk erosion, so that release is not only sustained but also provides desirable release rates. However, the pharmacokinetic release profile of these formulations may be first order, zero order, bi- or multi-phasic, to provide the desired reversible local anesthetic effect over the desired time period.

The controlled release material should be biocompatible. In the case of polymeric materials, biocompatibility is enhanced by recrystallization of either the monomers forming the polymer and/or the polymer Using standard techniques.

Suitable biodegradable polymers can be utilized as the controlled release material. The polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters or mixtures or blends of any of these. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. Preferred controlled release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers such as gelatin and fibrin and polysaccharides such as hyaluronic acid. Since polylactic acid takes at least one year to degrade in vivo, this polymer should be utilized by itself only in circumstances where such a degradation rate is desirable or acceptable.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 (Ludwig, et al.), the disclosure of which is hereby incorporated by reference in its entirety. In brief, Ludwig prepares such copolymers by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100 C. to about 250 C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

The substrates of the presently described formulations in certain preferred embodiments are manufactured using a method that evenly disperses the local anesthetic throughout the formulation, such as emulsion preparation, solvent casting, spray drying or hot melt, rather than a method such as compression molding. A desired release profile may be achieved by using a mixture of polymers having different release rates.

Methods for manufacture of microspheres are well known and are typified in the following examples. Examples of suitable methods of making microspheres include solvent evaporation, phase separation and fluidized bed coating.

In solvent evaporation procedures, the local anesthetic agent, if soluble in organic solvents, may be entrapped in the biodegradable polymer by dissolving the polymer in a volatile organic solvent, adding the drug to the organic phase, emulsifying the organic phase in water which contains less than 2% polyvinyl alcohol, and finally removing the solvent under vacuum to form discrete, hardened monolithic microspheres.

Phase separation microencapsulation procedures are suitable for entrapping water-soluble agents in the polymer to prepare microcapsules and microspheres. Phase separation involves coacervation of the polymer from an organic solvent by addition of a nonsolvent such as silicone oil. In a preferred embodiment, the microspheres may be prepared by the process of Ramstack et al., 1995, in published international patent application WO 95/13799, the disclosure of which is incorporated herein in its entirety. The Ramstack et al. process essentially provides for a first phase, including an active agent and a polymer, and a second phase, that are pumped through a static mixer into a quench liquid to form microparticles containing the active agent. The first and second phases can optionally be substantially immiscible and the second phase is preferably free from solvents for the polymer and the active agent and includes an aqueous solution of an emulsifier.

In fluidized bed coating, the drug is dissolved in an organic solvent along with the polymer. The solution is then processed, e.g., through a Wurster air suspension coating apparatus to form the final microcapsule product.

The present invention is contemplated to encompass all injectable formulations, e.g., the technologies described above, with the inclusion of an opioid antagonist, such that the opioid antagonist is released in a controlled-release manner along with the opioid agonist.

For example, injectable composition can comprise a plurality of substrates in a pharmaceutically acceptable medium for injection, said substrates comprising an effective amount of a biocompatible, biodegradable controlled release material comprising a polymer selected from the group consisting of polyanhydrides, copolymers of lactic acid and glycolic acid, poly(lactic) acid, poly(glycolic) acid, polyesters, polyorthoesters, proteins, polysaccharides and combinations thereof.

Controlled Release Oral Dosage Forms

The opioid agonist and antagonist combination may be formulated as a controlled-release oral dosage form, including tablets and capsules. In preferred embodiments, the controlled-release oral dosage form provides a controlled release of an opioid agonist and a controlled-release of an opioid antagonist, such that when the dosage form is administered to a human, the blood levels of the agonist is maintained throughout the dosing period at an analgesically effective level, and the antagonist at a level sufficient to decrease the side effects associated with the opioid agonist but not sufficient to negate the analgesic effect of the opioid agonist.

The term "release rate," as used in the application, refers to a rate at which a drug is released from the dosage form. The release pattern of a drug is a function of its properties, such as its physicochemical properties. Solubility is one such property. Since drug must be in solution before they can be absorbed into the body. The release rate of the drug from an oral dosage form may be measured, for example, by measuring the dissolution rate of the drug from the dosage form using an in vitro test method conducted under standardized conditions, e.g., U.S.P. paddle, 100 rpm in simulated gastric fluid for the first hour and thereafter in simulated intestinal fluid. For purposes of the present invention, release rate may be used as a surrogate measure of drug delivery in-vivo.

In certain embodiments of the present invention, the ratio of the opioid agonist to the antagonist in the controlled-release oral dosage form is about 1:1 to about 100:1 by weight. In preferred embodiments, the ratio of the opioid agonist with the antagonist is about 40:1 to about 50:1 by weight, more preferably about 20:1. In other preferred embodiments of the invention the amount of the opioid receptor antagonist administered is about 100 to about 1000 fold less than the amount of the opioid agonist administered Controlled-release oral dosage forms according the invention may be prepared using the methods available to one skilled in the art. In certain embodiments of the present invention, controlled-release tablets comprise the opioid agonist and antagonist in a controlled release matrix. The controlled-release matrix may include hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the opioid may be used in accordance with the present invention. The opioid agonist particles may, alternatively or additionally, be film coated with a material that permits release of the opioid agonist at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

The dosage forms comprising an opioid agonist and opioid antagonist may optionally be coated with one or more materials suitable for the regulation of the opioid agonist release or for the protection of the formulation. In one embodiment, coatings are provided to permit either pH-dependent or pH-independent release, e.g., when exposed to gastrointestinal fluid. A pH-dependent coating serves to release the opioid in desired areas of the gastrointestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release of the opioid regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the opioid agonist/opioid antagonist combination is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493, assigned to the Assignee of the present invention and hereby incorporated by reference.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate)copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit RL, 50% Eudragit RL and 50% Eudragit® RS, and 10% Eudragit® RL:Eudragit® 90% RS. Of course, one skilled in the art will recognize that other acrylic polymers may also be used, such as, for example, Eudragit® L.

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

When a hydrophobic controlled release coating material is used to coat inert pharmaceutical beads such as nu pariel 18/20 beads, which are already coated with an opioid agonist, a plurality of the resultant solid controlled release beads may thereafter be placed in a gelatin capsule, with the opioid antagonist in a substantially non-releasable form. The dosage form provides an effective controlled release dose of the opioid agonist when ingested and contacted by an environmental fluid, e.g., gastric fluid or dissolution media.

The controlled release bead formulations of the present invention slowly release the opioid agonist, e.g., when ingested and exposed to gastric fluids, and then to intestinal fluids. The controlled release profile of the formulations of the invention can be altered, for example, by varying the amount of overcoating with the hydrophobic material, altering the manner in which the plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with an opioid agonist may be prepared, e.g., by dissolving the drug in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Preformulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined controlled release of the opioid agonist and opioid antagonist when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose. The release-modifying agent may also comprise a semi-permeable polymer. In certain preferred embodiments, the release-modifying agent is selected from hydroxypropylmethylcellulose, lactose, metal stearates, and mixtures of any of the foregoing. The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the controlled release formulation is achieved via a matrix having a controlled release coating as set forth above. The present invention also comprises sustained-release tablets comprising an opioid agonist and opioid antagonist particles, wherein the agonist and the antagonist are dispersed in a controlled release matrix that affords in-vitro dissolution rates of the opioid agonist within the preferred ranges and that releases the opioid agonist in a pH-dependent or pH-independent manner. The materials suitable for inclusion in a controlled release matrix will depend on the method used to form the matrix.

For example, a matrix in addition to the opioid agonist and the oploid antagonist, may include hydrophilic and/or hydrophobic materials, such as gums, cellulose ethers, acrylic resins, protein derived materials. Such matrices may also include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes, and stearyl alcohol; and polyallcylene glycols. Of these polymers, acrylic polymers, especially Eudragit® RSPO—the cellulose ethers, especially hydroxyalkylcelluloses and carboxyallcylcelluloses, are preferred. The oral dosage form may contain between 1% and 80% (by weight) of at least one hydrophilic or hydrophobic material. When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon. In certain embodiments, the oral dosage form contains up to 60% (by weight) of at least one polyalkylene glycol as part of the controlled release matrix.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing. Preferred hydrophobic materials are water-insoluble with more or less pronounced hydrophilic and/or hydrophobic trends. Preferably, the hydrophobic materials useful in the invention have a melting point from about 30° to about 200° C., preferably from about 45° to about 90° C. The list is not meant to be exclusive, and any pharmaceutically acceptable hydrophobic material or hydrophilic material which is capable of imparting controlled release of the opioid agonist and opioid antagonist may be used in accordance with the present invention.

The hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

Suitable hydrophobic materials which may be used in accordance with the present invention include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

A combination of two or more hydrophobic materials may be included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

An example of a suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkylcellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opioid agonist/opioid antagonist; (b) mixing the hydroxyalkyl cellulose containing granules with at least one $C_{12}$–$C_{36}$ aliphatic alcohol; and (c) optionally, compressing and shaping the granules. Preferably, the granules are formed by wet granulating the hydroxyalkylcellulose/opioid agonist/opioid antagonist with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598, assigned to the Assignee of the present invention and hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients,* American Pharmaceutical Association (1986), incorporated by reference herein.

The preparation of a suitable melt-extruded matrix according to the present invention may, for example, include the steps of blending the opioid agonist, opioid antagonist, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The extrudate preferably has a diameter of from about 0.1 to about 5 mm and provides sustained release of the opioid agonist and antagonist for a time period of from about 8 to about 24 hours.

An optional process for preparing the melt extrusions of the present invention includes directly metering into an extruder a hydrophobic material, the opioid agonist and antagonist, and an optional binder; heating the homogenous mixture; extruding the homogenous mixture to thereby form strands; cooling the strands containing the homogeneous mixture; cutting the strands into particles having a size from about 0.1 mm to about 12 mm. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is combined with the coated opioid antagonist particles and compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553–1593 (1980), incorporated by reference herein.

In yet another preferred embodiment, the extrudate can be shaped into tablets as set forth in U.S. Pat. No. 4,957,681 (Klimesch, et al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opioid analgesic compound utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release opioid agonist for prompt therapeutic effect. The immediate release opioid agonist may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the opioid agonist, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the opioid agonist and/or coated opioid antagonist particles, which are added thereafter to the extrudate. Such formulations typically will have the drugs blended together with the extruded matrix material, and then the mixture would be tableted in order to provide a slow release of the opioid agonist. Such formulations may be advantageous, for example, when the therapeutically active agent included in the formulation is sensitive to temperatures needed for softening the hydrophobic material and/or the retardant material.

In certain embodiments, the opioid antagonist is present as granulates comprising the opioid antagonist dispersed in a first controlled release matrix, and the opioid agonist is present as granulates comprising the opioid agonist dispersed in a second controlled-release matrix, the first controlled-release matrix providing controlled-release of the opioid antagonist and the second matrix providing controlled-release of the opioid agonist. In certain preferred embodiments, the first and second matrices cause the opioid agonist and the opioid antagonist to be released at substantially the same rate. In other embodiments, the opioid antagonist is prepared as granulates comprising the antagonist dispersed in a controlled-release matrix, said granulates being combined with the opioid agonist and a further controlled release material, such that the opioid antagonist and opioid agoinst are preferably released at substantially the same rate.

Additional Drugs

The oral dosage form of the present invention may further include, in addition to an opioid agonist and antagonist, one or more drugs that may or may not act synergistically therewith. Thus, in certain embodiments, a combination of two opioid agonists may be included in the dosage form, in addition to the opioid antagonist. For example, the dosage form may include two opioid agonist having different properties, such as half-life, solubility, potency, and a combination of any of the foregoing. In yet further embodiments, one or more opioid agonist is included and a further non-opioid drug is also included, in addition to the opioid antagonist. Such non-opioid drugs would preferably provide additional analgesia, and include, for example, aspirin, acetaminophen; non-steroidal anti-inflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cycooxygenase-II inhibitors ("COX II inhibitors"); and/or glycine receptor antagonists.

In certain preferred embodiments of the present invention, the invention allows for the use of lower doses of the opioid analgesic by virtue of the inclusion of an additional non-opioid agonist, such as an NSAID or a COX-2 inhibitor. By using lower amounts of either or both drugs, the side effects associated with effective pain management in humans are reduced.

Suitable non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$, a phenothiazine such as trifluoperazine or a naphthalene-sulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al.), all of which are hereby incorporated by reference. The NMDA antagonist may be included alone, or in combination with a local anesthetic such as lidocaine, as described in these Mayer, et.al. patents.

The treatment of chronic pain via the use of glycine receptor antagonists and the identification of such drugs is described in U.S. Pat. No. 5,514,680 (Weber, et al.), hereby incorporated by reference.

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain preferred COX-2 inhibitors include celecoxib (SC-58635), DUP-697, flosulide (CGP-28238), meloxicam, 6-methoxy-2 naphthylacetic acid (6-MNA), MK-966 (also known as Vioxx), nabumetone (prodrug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic.

In yet further embodiments, a non-opioid drug can be included which provides a desired effect other than analgesia, e.g., antitussive, expectorant, decongestant, antihistamine drugs, local anesthetics, and the like.

In certain preferred embodiments of the invention, the controlled release oral dosage form comprises an opioid agonist and an opioid antagonist in combination with acetominophen.

Acetaminophen is an analgesic/antipyretic drug which has been utilized for treating mild to moderate pain such as headache, neuralgia, and musculoskeletal pain. The recommended daily adult dose is about 325 to about 650 mg every 4 hours, not to exceed a total dose of 4 g in 24 hours. The maximum dose of immediate release acetaminophen is generally considered to be about 1000 mg.

It is contemplated that the combination formulations and methods of the present invention may include such acetaminophen doses as those set forth above, or lower doses per 4 hour dosing interval. Thus, it is possible that controlled release formulations prepared in accordance with the present invention include a greater total acetominophen dose than the 325–650 mg dose, but that dose will be released in a controlled-release manner over a longer dosing interval (e.g., over 8 hours or more).

It is contemplated that the dosage of acetaminophen and opioid agonist in the formulations and method of the present invention may be similar or the same as dosages which are already commercially available and accepted by clinicians. Acetaminophen is commercially available in the United States in fixed combination with opioid agonists, namely, codeine, oxycodone and hydrocodone. Typical oral capsule dosages of acetaminophen/codeine combinations include 325 mg acetaminophen and 15 mg codeine phosphate, 325 mg acetaminophen and 30 mg codeine phosphate and 325 mg acetaminophen and 60 mg codeine phosphate. Tablets typically include 300 mg acetaminophen and 7.5 mg codeine phosphate, 300 mg acetaminophen and 15 mg codeine phosphate, 300 mg acetaminophen and 30 mg codeine phosphate, and 300 mg acetaminophen and 60 mg codeine phosphate.

Hydrocodone/acetaminophen capsules are typically available in fixed combinations of 5 mg hydrocodone (as the bitartrate salt) and 500 mg acetaminophen. Hydrocodone/acetaminophen tablets are typically available in fixed combinations of 500 mg acetaminophen and 2.5 mg hydrocodone bitartrate, 500 mg acetaminophen and 5 mg hydrocodone bitartrate, 500 mg acetaminophen and 7.5 mg hydrocodone, 7.5 mg hydrocodone bitartrate and 650 or 750 mg acetaminophen, and 10 mg hydrocodone bitartrate and 500, 650, 660 mg acetaminophen. Oxycodone/acetaminophen capsules and caplets are available in fixed combination of 5 mg oxycodone (as the hydrochloride salt) and 500 mg acetaminophen, and in tablets as 5 mg oxycodone hydrochloride and 325 mg acetaminophen.

The fixed combinations described above are for information purposes only and are not meant to limit the possible relative amounts of opioid and acetaminophen contained in the formulations encompassed within the present invention. As disclosed herein and in accordance with the present invention, it is contemplated that in certain embodiments, the opioid agonist/opioid antagonist/acetaminophen combinations encompassed herein will have greater or lesser dosages of either the opioid agonist or acetaminophen, and that the ratio of opioid agonist to acetaminophen will vary based on the particular opioid agonist and opioid antagonist chosen for a formulation and the amount of opioid antagonist included therein, among other things.

In certain preferred embodiments, the oral dosage form comprises an opioid agonist (hydrocodone or oxycodone) and opioid antagonist (naltrexone, naloxone and nalmefene) and acetaminophen.

In yet further embodiments, a non-opioid drug can be included which provides a desired effect other than analgesia, e.g., antitussive, expectorant, decongestant, antihistamine drugs, local anesthetics, and the like.

All of the documents cited in this application are incorporated herein by reference in their entireties.

DETAILED DESCRIPTION OF CERTAIN PREFERRED EMBODIMENTS

The following examples illustrate various aspects of the present invention. They are not to be construed to limit the claims in any manner whatsoever.

EXAMPLE 1

Controlled Release Morphine/Naltrexone Beads

The objective of this Example is to prepare a controlled release naltrexone bead (antagonist) to be incorporated into controlled release opioid products (agonist).

Morphine/Naltrexone CR capsule

A Naltrexone controlled release bead (NXCR) is developed which can be incorporated into hard gelatin capsules containing other opioid controlled release beads. Morphine sulfate controlled release beads (MSCR) is formulated as an example to be mixed with NXCR beads and the mixture is encapsulated.

Formula 1A. NXCR beads

| Ingredients | | Amt/unit* (mg) | Amt/batch (g) |
|---|---|---|---|
| Step 1. Drug layering | Naltrexone HCl | 2.0 | 14.0 |
| | Non-pareil beads (30/35 mesh) | 96.0 | 672.0 |
| | Plasdone C30 | 1.0 | 7.0 |
| | Talc | 1.0 | 7.0 |
| | Water | | 280 |
| Step 2. Seal coat | Opadry Clear (Hydroypropylmethyl cellulose) | 5.0 | 35.0 |
| | Water | | 315.0 |
| Step 3. Sustained release coat | Eudragit RS30D (dry) | 13.23 | 92.61 |
| | Tributyl citrate | 3.51 | 24.57 |
| | Tween 80 | 0.03 | 0.21 |
| | Talc | 13.23 | 92.61 |
| | Water | | 624.0 |
| Step 4. Seal coat | Opadry Clear (Hydroxypropylmethyl cellulose) | 5.0 | 35.0 |
| | Water | | 315.0 |
| Total | | 140 | 980 |

Bead Manufacturing Procedure (NXCR beads)

1. Dissolve naltrexone HCl and plasdone in water. Spray the drug solution onto non-pareil beads in a fluid bed coater with Wurster insert. Spray Opadry clear solution as seal coat.
2. Spray Opadry Clear onto the drug loaded beads as seal coat in the fluid bed coater.
3. Disperse Eudragit RS30D, tributyl citrate, Tween 80 and talc in water. Spray the dispersion onto the beads in the fluid bed coater.
4. Dissolve Opadry Clear in water. Spray the solution onto the beads in the fluid bed coater.
5. Cure the beads at 60° C./for 24 hours.

Dissolution Method

1. Apparatus—USP Type II (paddle), 50 rpm at 37° C.
2. Sampling time—1, 2, 4, 12, 24, and 36 hours.
3. Media—900 ml pH 6.5 phosphate buffer.
4. Analytical method—High performance liquid chromatography.

Results and Discussion

The NXCR beads were found to have the following dissolution results:

| | Time (hr) | | | | |
|---|---|---|---|---|---|
| | 1 | 4 | 8 | 12 | 18 |
| Mean % dissolved | 10 | 13 | 24 | 40 | 75 | nd = none detected

The dissolution results show that the drug release rate of naltrexone could be suitable for dosing every 24 hours.

Formula 1B (Formulation for the Morphine beads—MSCR beads)

| Ingredients | | Amt/unit* (mg) | Amt/batch (kg) |
|---|---|---|---|
| Step 1. Drug loading | Morphine sulfate | 60.0 | 45.0 |
| | Lactose impalpable | 12.0 | 9.0 |
| | Eudragit RS30D (dry) | 2.0 | 1.5 |
| | Povidone | 3.5 | 2.63 |
| | Nupareil PG 30/35 | 16.8 | 12.6 |
| | Opadry blue | 4.9 | 3.68 |
| | Water | | 31.5 |
| Step 2. Controlled Release Coat | MSIR beads (step 1) | 99.2 | 74.41 |
| | Eudragit RS 30D (dry) | 4.712 | 3.53 |
| | Eudragit RL 30D (dry) | 0.248 | 0.19 |
| | Triethyl citrate | 0.992 | 0.74 |
| | Talc | 1.884 | 1.49 |
| | Opadry blue | 5.639 | 4.23 |
| | Water | | q.s. |
| Total | | 112.675 | 159 |

Manufacturing Procedure (MSCR beads)

1. Disperse povidone and Eudragit RS30D in water. Blend morphine sulfate and lactose.
2. Load beads in Rotor processor. Spray the drug powder blend and the binder solution onto beads.
3. Film-coat the above beads in the Rotor processor.
4. Disperse Eudragit RS30D, RL 30D, Triethyl citrate, talc and triehtyl citrate in water. Coat the above beads in a fluid bed coated with Wurster insert.
5. Cure the beads.

Dissolution Method

1. Apparatus—USP Type II (paddle), 100 rpm at 37° C.
2. Sampling time—1, 2, 4, 12, 24, and 36 hours.
3. Media—700 ml SGF for first 55 min then converted to 900 ml SIF
4. Analytical method—High performance liquid chromatography.

Results and Discussion

The MSCR beads were found to have the following dissolution results:

| | Time (hr) | | | | | |
|---|---|---|---|---|---|---|
| | 1 | 2 | 4 | 8 | 12 | 18 | 24 |
| Mean % dissolved | 4 | 8 | 23 | 49 | 70 | 83 | 85 | nd = none detected

The dissolution results show that the drug release rate of morphine sulfate could be suitable for dosing every 24 hours.

Example 1C. Morphine CR/Naltrexone CR Capsule

| | Ingredients | Amt/unit* (mg) | Amt/batch (kg) |
|---|---|---|---|
| Step 1. Encapsulation | Morphine sulfate CR beads | 112.675 | 159 |
| | Naltrexone HCl CR beads | 140.0 | 105 |
| Total | | 232.675 | 264 |

Manufacturing Procedure (MSCR/NXCR Capsule)

Fill 112.675 mg of the MSCR beads (Example 1B) and 140 mg of the naltrexone CR beads (Example 1A) into a suitable sized capsule.

EXAMPLE 2

Hydromorphone/Naltrexone CR capsule

Naltrexone controlled release pellets are developed which can be incorporated into hard gelatin capsules containing other opioid controlled release pellets. Hydromorphone HCl controlled release pellets (HHCR) are formulated as an example to be mixed with Naltrexone CR pellets and the mixture is encapsulated.

Formula 2A Naltrexone HCl CR Pellets

| Ingredient | Amt/unit (mg) | Amt/batch (gm) |
|---|---|---|
| Naltrexone HCl | 2.0 | 33.3 |
| Eudragit RSPO | 70.0 | 1166.7 |
| Eudragit RLPO | 8.0 | 133.3 |
| Stearic Acid | 40.0 | 666.7 |
| Total | 120.0 | 2000.0 |

Process
1. Blend Naltrexone HCl, Eudragit RSPO, Eudragit RLPO, and Stearic Acid in a twin shell blender.
2. Continuously feed the blended material into a twin screw extruder and collect the resultant strands on a conveyor.
3. Allow the strands to cool a Conveyor.
4. Cut the cooled strands into pellets using a Pelletizer.
5. Screen the pellets and collect desired sieve portion.

Dissolution Method
1. Apparatus—USP Type I (Basket), 75 rpm at 37° C.
2. Sampling Time: 1, 2, 4, 8, 12
3. Media: 700 mL of SGF for one hour/900 mL SIF thereafter
4. Analytical Method: High Performance Liquid Chromatography Results

|  | Time (hour) | | | | |
|---|---|---|---|---|---|
|  | 1 | 2 | 4 | 8 | 12 |
| Mean % Dissolved | 13.9 | 20.3 | 27.3 | 37.6 | 45.3 |

Formula 2B (Hydromorphone HCl CR Pellets)

| Ingredient | Amt/unit (mg) | Amt/batch (Kg) |
|---|---|---|
| Hydromorphone HCl | 12.0 | 3.2 |
| Eudragit RSPO | 76.5 | 20.4 |
| Ethylcellulose | 4.5 | 1.2 |
| Stearyl Alcohol | 27.0 | 7.2 |
| Total | 120.0 | 32.0 |

Process
1. Pass Stearyl Alcohol flakes through an impact mill.
2. Blend the Hydromorphone HCl, Eudragit, Ethycellulose and milled Stearyl Alcohol in a twin shell blender.
3. Continuously feed the blended material into a twin screw extruder and collect the resultant strands on a conveyor.
4. Allow the strands to cool a Conveyor.
5. Cut the cooled strands into pellets using a Pelletizer.
6. Screen the pellets and collect desired sieve portion.

Dissolution Method
1. Apparatus—USP Type I (Basket), 100 rpm at 37° C.
2. Sampling Time: 1, 2, 4, 8, 12, 18, 24
3. Media: 900 mL (USP) SIF+3 g NaCl/L
4. Analytical Method: High Performance Liquid Chromatography Results

|  | Time (hour) | | | | | | |
|---|---|---|---|---|---|---|---|
|  | 1 | 2 | 4 | 8 | 12 | 18 | 24 |
| Mean % Dissolved | 12.6 | 23.8 | 43.2 | 69.5 | 84.7 | 96.5 | 100.8 |

Formula 2C. Hydromorphone HCl CR/Naltrexone CR Capsule

| Ingredients | Amt/unit (mg) | Amt/batch (kg) |
|---|---|---|
| Hydromorphone HCl CR Pellets | 120.0 | 12.0 |
| Naltrexone HCl CR Pellets | 120.0 | 12.0 |
| Total | 240.0 | 24.0 |

Process
1. Fill 120.0 mg of Hydromorphone HCl CR Pellets (Example 3B) and 120 mg of the Naltrexone HCl CR Pellets (Example 3A) into a suitable sized capsule.

EXAMPLE 3

CR Opioid Agonist/Antagonist Granulate (Tableted)

Controlled release tablets containing an opioid agonist (oxycodone HCl) and opioid antagonist (naltrexone HCl) are prepared in which both drugs are present as granulates, the granulates comprising the opioid agonist and the antagonist dispersed in a controlled release matrix. The granulates are combined with melted wax (stearyl alcohol) to produce waxed granulates, which are then milled and mixed with other excipients and compressed into tablets.

| Ingredient | Amt/unit (mg) | Amt/batch (kg) |
|---|---|---|
| Oxycodone HCl | 10.00 | 11.00 |
| Naltrexone HCl | 0.50 | 0.55 |
| Spray Dried Lactose | 68.75 | 75.62 |
| Povidone | 5.00 | 5.50 |
| Eudragit RS 30D (dry wt.) | 10.00 | 11.00 |
| Triacetin | 2.00 | 2.20 |
| Stearyl Alcohol | 25.00 | 27.50 |
| Talc | 2.50 | 2.75 |
| Magnesium Stearate | 1.25 | 1.38 |
| Opadry White | 5.00 | 5.50 |
| Purified Water |  | 31.16* |
| Total | 130.00 | 143.00 |

*Remains in product as residual moisture only.

Process

1. Solution Preparation  Plasticize the Eudragit with Triacetin by mixing. Dissolve Naltrexone HCl into the plasticized solution.

-continued

| | |
|---|---|
| 2. Granulation | Place Oxycodone HCl, Spray Dried Lactose, and Povidone into a fluid bed granulator and apply the above solution. |
| 3. Milling | Pass the granulation through a rotating impeller mill. |
| 4. Drying | Dry granulation if moisture content is too high. |
| 5. Waxing | Melt Stearyl Alcohol and wax the above granulation by adding melted Stearyl Alcohol onto granulation while mixing. |
| 6. Cooling | Cool the waxed granulation in a fluid bed dryer. |
| 7. Milling | Pass the cooled waxed granulation through a rotating impeller mill. |
| 8. Blending | Blend the milled waxed granulation, Talc and Magnesium Stearate. |
| 9. Compression | Compress the resultant granulation using a tablet press. |
| 10. Coating | Prepare a film coating solution by dispersing the Opadry in Purified Water and applying it to the tablet cores. |

EXAMPLE 4

CR Opioid Agonist/Antagonist Granulate (Tableted)

Controlled release tablets containing an opioid agonist (morphine sulfate) and opioid antagonist (naltrexone HCl) are prepared. The controlled release tablets comprise granulates comprising the opioid agonist and the antagonist dispersed in a controlled-release matrix. The granulates are combined with melted wax (cetostearyl alcohol) to produce waxed granulates, which are then milled and mixed with other excipients and compressed into tablets.

| Ingredient | Amt/unit (mg) | Amt/batch (kg) |
|---|---|---|
| Morphine Sulfate (pentahydrate) | 30.00 | 108.0 |
| Naltrexone HCl | 0.50 | 1.8 |
| Spray Dried Lactose | 69.5 | 250.2 |
| Hydroxyethyl Cellulose | 10.0 | 36.0 |
| Purified Water | | 75.9* |
| Cetostearyl Alcohol | 35.0 | 126.0 |
| Talc | 3.0 | 10.8 |
| Magnesium Stearate | 2.0 | 7.2 |
| Opadry Purple | 3.0 | 10.8 |
| Purified Water | | 61.2* |
| Total | 153.0 | 550.8 |

*Remains in product as residual moisture only.

Process

| | |
|---|---|
| 1. Solution Preparation | Dissolve Naltrexone HCl in Purified Water by mixing. |
| 2. Granulation | Place Morphine Sulfate, Spray Dried Lactose, and Hydroxyethyl Cellulose in a mixer and granulate with Naltrexone HCl solution above. |
| 3. Drying | Dry the above granulation in a fluid bed dryer. |
| 4. Milling | Pass the granulation through a mill. |
| 5. Drying | Dry granulation if moisture content is too high. |
| 6. Waxing | Melt Cetostearyl Alcohol and wax the above granulation by adding melted Cetostearyl Alcohol onto granulation while mixing. |
| 7. Cooling | Cool the waxed granulation in a fluid bed dryer. |
| 8. Milling | Pass the cooled waxed granulation through a mill. |
| 9. Blending | Blend the milled waxed granulation, Talc and Magnesium Stearate. |
| 10. Compression | Compress the resultant granulation using a tablet press. |
| 11. Coating | Prepare a film coating solution by dispersing the Opadry in Purified Water and applying it to the tablet cores. |

EXAMPLE 5

Tableted CR Opioid Agonist/Antagonist Extrudate

Controlled-release capsules containing an opioid agonist (hydromorphone HCl) and opioid antagonist (naltrexone) are prepared. Extruded drug-containing pellets are prepared by combining a wax with ethylcellulose and Eudragit and feeding the mixture into a twin screw extruder. The pellets are then filled into hard gelatin capsules.

Formula

| Ingredient | Amt/unit (mg) | Amt/batch (gm) |
|---|---|---|
| Hydromorphone HCl | 12.0 | 120.0 |
| Eudragit RSPO | 76.0 | 760.0 |
| Ethylcellulose | 4.5 | 45.0 |
| Stearyl Alcohol | 27.0 | 270.0 |
| Naltrexone HCl | 0.5 | 5.0 |
| Hard Gelatin Capsules | √ | √ |
| Total | 120.0 | 1200.0 |

Process

| | |
|---|---|
| 1. Milling | Pass stearyl alcohol flakes through an impact mill. |
| 2. Blending | Mix Hydromorphone HCl, Eudragit, Ethylcellulose, milled Stearyl Alcohol, and Naltrexone HCl in a twin shell blender. |
| 3. Extrusion | Continuously feed the blended material into a twin screw extruder and collect the resultant strands on a conveyor. |
| 4. Cooling | Allow the strands to cool a Conveyor. |
| 5. Pelletizing | Cut the cooled strands into pellets using a Pelletizer. |
| 6. Screening | Screen the pellets and collect desired sieve portion. |
| 7. Encapsulation | Fill the extruded pellets into hard gelatin capsules at 120 mg. |

EXAMPLE 6

Tableted CR Opioid Agonist/Antagonist Extrudate

Controlled-release tablets containing an opioid agonist (hydrocodone bitartrate) and opioid antagonist (naltrexone HCl) are prepared. The tablets contain the drugs in the form of extruded pellets.

Formula

| Ingredient | Amt/unit (mg) | Amt/batch (kg) |
|---|---|---|
| Hydrocodone Bitartrate | 30.0 | 15.0 |
| Naltrexone HCl | 0.5 | 0.25 |
| Stearyl Alcohol | 44.0 | 22.0 |
| Anhydrous Dicalcium Phosphate (Powdered) | 62.0 | 31.0 |

-continued

| Ingredient | Amt/unit (mg) | Amt/batch (kg) |
|---|---|---|
| Microcrystalline Cellulose | 62.0 | 31.0 |
| Glyceryl Behenate | 20.0 | 10.0 |
| Magnesium Stearate | 2.0 | 1.0 |
| Opadry Red | 10.0 | 5.0 |
| Purified Water |  | 28.4* |
| Total | 230.5 | 115.25 |

*Remains in product as residual moisture only.

Process

| 1. Milling | Pass the Stearyl Alcohol flakes through an occillating mill. |
|---|---|
| 2. Blending | Mix the Hydrocodone Bitartrate, Naloxone HCl, milled Stearyl Alcohol, Anhydrous Dicalcium Phosphate, Microcrystalline Cellulose, and Glyceryl Behenate in a twin shell blender. |
| 3. Extrusion | Continuously feed the blended material into a twin screw extruder and collect the resultant heated material on a conveyor. |
| 4. Cooling | Allow the extrudate to cool on the conveyor. |
| 5. Milling | Mill the cooled extrudate using an occillating mill. |
| 6. Blending | Blend the milled extrudate and Magnesium Stearate. |
| 7. Compression | Compress the resultant granulation using a tablet press. |
| 8. Coating | Prepare a film coating solution by dispersing the Opadry in Purified Water and applying it to the tablet cores. |

EXAMPLE 7

Tableted CR Opioid Agonist/Antagonist (Modified Release)

Controlled release tablets containing an opioid agonist (morphine sulfate) and opioid antagonist (naltrexone HCl) are prepared. In this Example, opioid antagonist is treated with a controlled-release carrier (Eudragit RS 30D) to modify its release rate before it is combined with the opioid agonist and formulated into a controlled-release tablet.

Formula

| Ingredient | Amt/unit (mg) | Amt/batch (kg) |
|---|---|---|
| Naltrexone HCl | 0.50 | 1.80 |
| Eudragit RS 30D (dry wt.) | 0.03 | 0.10 |
| Triacetin | 0.01 | 0.04 |
| Morphine Sulfate (pentahydrate) | 30.00 | 108.00 |
| Spray Dried Lactose | 69.46 | 250.06 |
| Hydroxyethyl Cellulose | 10.00 | 36.00 |
| Purified Water |  | 75.90* |
| Cetostearyl Alcohol | 35.00 | 126.00 |
| Talc | 3.00 | 10.80 |
| Magnesium Stearate | 2.00 | 7.20 |
| Opadry Purple | 3.00 | 10.80 |
| Purified Water |  | 61.20* |
| Total | 153.0 | 550.8 |

*Remains in product as residual moisture only.

Process

| 1. Solution Preparation | Plasticize the Eudragit by mixing with Triacetin. |
|---|---|
| 2. Pre-Granulation | Pre-granulate the Naltrexone HCl in a fluid bed granulator by applying the above solution. |
| 3. Granulation | Place Naltrexone HCl granulation (from above), Morphine Sulfate, Spray Dried Lactose, and Hydroxyethyl Cellulose in a mixer and granulate with Purified Water. |
| 4. Drying | Dry the above granulation in a fluid bed dryer. |
| 5. Milling | Pass the granulation through a mill. |
| 6. Drying | Dry granulation if moisture content is too high. |
| 7. Waxing | Melt Cetostearyl Alcohol and wax the above granulation by adding melted Cetostearyl Alcohol onto granulation while mixing. |
| 8. Cooling | Cool the waxed granulation in a fluid bed dryer. |
| 9. Milling | Pass the cooled waxed granulation through a mill. |
| 10. Blending | Blend the milled waxed granulation, Talc and Magnesium Stearate. |
| 11. Compression | Compress the resultant granulation using a tablet press. |
| 12. Coating | Prepare a film coating solution by dispersing the Opadry in Purified Water and applying it to the tablet cores. |

EXAMPLE 8

Transdermal Delivery System

A transdermal patch is prepared in accordance with the disclosure of WO 96/19975 for Example 1 therein as follows, with the modification that a requisite amount of naltrexone is included: 1.139 g of a 47.83 w/% polyacrylate solution with a selfnetting acrylate copolymers containing 2-ethylhexylacrylates, vinyl acetates, acrylic acid (dissolving agent:ethylacetate:heptan:isopropanol:toluol:acetylacetonate in the ratio of 37:26:26:4:1), 100 g laevulinic acid, 150 g oleyloleate, 100 g polyvinylpyrollidone, 150 g ethanol, 200 g ethyl acetate and 100 g buprenorphine base and 1 g naltrexone are homogenized. The mixture is stirred for about 2 hours and then examined visually to determine if all solid substances have been dissolved. One has to control the evaporation loss by method of weighing back and makes up for the solvent with the help of ethylacetate, if necessary. Thereafter, the mixture is put onto a 420 mm wide, transparent polyester foil, since the surface weight of the dried layer of paste is 80 g per m.sup.2. The polyester foil which can be dissolved again with treatment of silicone serves as a protective layer. The solvent is removed by drying with heated air which is led over a moist lane. With this treatment of warmth not only do solvents evaporate but the the laevulinic acid melts as well. Thereafter, the sealing film is covered with a polyester foil 15 .mu.ab. A surface of about 16 cm$^2$ is cut with the help of the appropriate cutting tool, and the rims that have been left between the individual systems are removed.

EXAMPLE 9

The formulation utilized for Example 8 is substantially the same as that described in Example 3 of WO 96/19975, which is prepared in accordance with Example 8 and is stated therein to include 10% buprenorphine (with a proportional amount of naltrexone as set forth in Example above), 10% levulinic acid, 10% polyvinylpyrollidone, 10% oleyloeate, the remainder comprising polyacrylate. In order to achieve the nominal delivery rate of 25 ug/hr expected for the formulation of Example 1, the total of buprenorphine included in the transdermal patch is about 10 mg, the active surface area is about 12.5 cm$^2$ and the patch size may be, e.g., about 30.6 cm$^2$.

The dosing regimen was one (1) patch containing 10 mg buprenorphine base and 0.1 mg naltrexone/patch reservoir applied to the subject's skin and maintained in contact with the skin for a time period of seven (7) days.

EXAMPLE 10

Transdermal Device

The following ingredients are used in making the pharmaceutical-containing polymer matrix discs: active agent, 10 parts (consisting of hydromorphone and naltrexone in a 10:1 ratio); DC-360 polysiloxane medical fluid (20 cps), 10 parts; silicone (medical-grade) 382 elastomer, 80 parts; catalyst M, 20 drops per 100 g. of the mixture.

The active agent is thoroughly dispersed in the 80 parts of Silastic medical-grade 382 elastomer by using a high torque mixer (sold by Cole-Parmer Company) at about 1000 RPM.

With continued agitation, 20 parts of DC-360 (silicone medical fluid) and 20 drops (for every 100 g of the mixture) of a cross-linking agent, designated as catalyst M, which is stannous octanoate, are added to the active agent-elastomer microdispersed mixture. After each addition of the mixture, material is thoroughly mixed, and the dispersed mixture is placed under vacuum to remove entrapped air.

The active agent-polydimethylsiloxane dispersion is placed into a device maker and is cross-linked at an elevated temperature (25 degrees–100 degrees C.) to form a cross-linked, medicated polymer sheet, which has a thickness of 0.2–3 mm.

The medicated polymer sheet is removed from the device maker and is cut into circular discs of about 3–20 sq. cm. The discs are attached to a backing layer of heat sealable polyester film which is laminated to aluminum foil. This laminate is sold by 3M Company as Scotchpak 1006. The medicated discs are attached using an adhesive polymer solution, which is a silicone adhesive polymer sold by Dow Corning as DC-355. Alternately, the discs can be formed directly on the backing layer.

The skin permeation enhancer-adhesive film is made using the following ingredients: skin permeation enhancer, 6.5 parts; acetone 30 parts; and adhesive polymer solution, 100 parts. The skin permeation enhancer-adhesive layer is made by dissolving the 6.5 parts by weight of a skin permeation enhancer in 30 parts of acetone. The acetone solution then is added to 100 parts of a silicone adhesive solution sold by Dow-Corning under the designation DC-355.

The mixture is thoroughly mixed to form a homogeneous mixture of skin permeation enhancer and adhesive polymer, which is applied to a strip of a release liner which is a siliconized, or a Teflon-coated polyester film to permit easy removal of the release liner just prior to application of the final polymer matrix disc dosage unit to the subject to be transdermally treated. The adhesive mixture is applied at a controlled thickness. The formed layer has a thickness of about 50–200 microns. The layer is dried completely in vacuum to remove volatile matter.

The skin permeation enhancer-adhesive polymer layer with release liner is applied onto the active agent-containing polymer matrix disc with the attached backing layer under a constant pressure to provide a firmly adhered strip of a four-layered structure as follows:
1. Backing layer
2. Active agent-containing polymer matrix layer
3. Skin permeation enhancer-adhesive layer
4. Release film layer which can be readily removed to permit application to the skin of the subject to receive transdermally the active agent.

By use of an appropriate cutter, the strip is cut to provide the transdermal polymer matrix dosage units which are circular in shape and have an area of about 10 sq. cm.

The above polymer matrix disc dosage units are made using the following skin permeation enhancers: 1-dodecylazacycloheptan-2-one (sold under the trademark Azone), propyl myristate and propyl oleate.

The transdermal absorption of the active agent from the polymer matrix dosage units of this invention is evaluated by using a skin specimen from a "hairless" mouse or human cadaver by following the procedure described by P. R. Keshary and Y. W. Chien, in Drug Develop. & Ind. Pharm., 10 (6) 883–913 (1984).

EXAMPLE 11

Oral Mucosal Delivery System

Oral mucosal patches are prepared by homogeneously mixing buprenorphine free base and naltrexone (8%, in a 20:1 ratio), Carbopol 934 (52%), polyisobutylene (35%) and polyisoprene (5%, w/w) via a two-roll mill and then compressing the mixture to the appropriate thickness. A membrane backing (ethylcellulose) is applied to one side of the compressed material and then circular disks (0.5 cm$^2$) are punched from the material. The backing is included in order to retard drug release from one side of the disk and to prohibit adhesion to opposing side tissues. Each soft, flexible disk is approximately 0.6 mm thick and contains approximately 3 mg buprenorphine and an appropriate amount of naltrexone. The patches are suitable for gum and lip application.

EXAMPLES 12–14

Suppositories

Morphine and naltrexone were tested in the controlled release system of the invention.

The following three suppository formulations set forth in Table 1 demonstrate the principle of the invention with regard to a controlled release suppository:

TABLE 1

Morphine Suppository Formulations

| INGREDIENT | EXAMPLE | | |
| --- | --- | --- | --- |
|  | 1 | 2 | 3 |
| Morphine Sulphate | 30.0 mg | 30.0 mg | 30.0 mg |
| Naltrexone HCL | .5 mg | .5 mg | .5 mg |
| Sodium Alginate (low viscosity LF grade) | 327 mg | 409 mg | 450 mg |
| DiCalcium phosphate | 32.5 mg | 40.5 mg | 45.0 mg |
| Novata-B | 1410.0 mg | 1320.0 mg | 1275.0 mg |
| Total | 1800.0 mg | 1800.0 mg | 1800.0 mg |

Novata-B is a mixture of mono-, di- and triglycerides based on saturated natural fatty acids of the chain lengths $C_{12}$ to $C_{18}$, with a specific melting range (33.4 degrees C.-25.5 degrees C.).

The suppositories were prepared according to the following method: morphine sulphate powder, naltrexone HCl powder, sodium alginate and calcium phosphate were all passed through a #200 sieve, individually. All three powders were intimately mixed in a suitable mixing apparatus. Novata B was melted in a stainless steel pot, keeping the temperature below 60 degrees C.

The mixed powder was then added to the completely melted wax (around 50 degrees C.) with constant stirring. The temperature was then cooled slowly to 40 degrees C. and kept constant at that temperature. The uniform suspension was then transferred to a automated suppository filing kettle, and continuously stirred at 38 degrees C.

After the fill weight was determined, the suppository shells were filled to the suggested fill weight at a temperature of about 37 degrees C./(e.g., between 36 degrees–38 degrees C.). The suppositories were allowed to cool, then sealed.

EXAMPLES 15–19

Compositions for Nasal Administration

In Examples 15–19, formulations exemplified in U.S. Pat. No. 5,629,011 are modified in order to include an opioid antagonist, in accordance with the present invention.

In Example 15, a bioadhesive powder formulation of morphine-6-glucuronide and naltrexone is prepared using microspheres of cross-linked starch. The microspheres are prepared by the method described in EP 223302. A preferred size of microspheres is 1–100 µm. The formulation may be prepared by dissolving 75 mg of the agonist and a sufficient amount of naltrexone in 30 ml water and mixed with 1 g of starch microspheres. The product is freeze-dried to produce a free flowing powder. The powder can be administered to the nasal cavity using an insufflator device.

In Example 16, the bioadhesive microsphere system disclosed in Example 15 are prepared but in addition an absorption enhancing agent is employed. A preferred material is lysophosphatidyl glycerol (LPG). 100 mg LPG is added to the suspension of the morphine metabolite and microspheres.

In Example 17, a liquid formulation is prepared with added absorption enhancing agent as follows: 150 mg of morphine-6-glucuronide and a sufficient amount of naltrexone are dissolved in 10 ml of a 0.5% solution of medium viscosity grade of Chitosan (80% degree of deacetylation, Protan Limited). The substituted cyclodextrin material dimethyl-.beta.-cyclodextrin (Sigma Chemical Comp) is added to provide a concentration of 5%. The liquid formulation can be administered using a conventional pump spray device.

In Example 18, the formulation disclosed in Example 17 is prepared but in the place of the dimethyl-beta-cyclodextrin, alpha-cyclodextrin (Sigma Chemical Co.) at the same concentration of 50 mg/ml is added.

In Example 19, the microsphere formulation described in Example 16 is prepared but instead of the enhancing agent, a chelating agent in the form of EDTA is employed. 50 mg of EDTA is added to the suspension of morphine metabolite and microspheres. The product is freeze dried as detailed in Example 15.

EXAMPLE 20

Microspheres for Injection

In Examples 20, buprenorphine/naltrexone microspheres are prepared by dissolving the agents and the polymer in ethyl acetate. The polymer is 50:50 poly (D,L) lactic co-glycolic acid which has a mole percent composition of 50% lactide and 50% glycolide. This dispersed phase is then added to a solution of polyvinyl alcohol (PVA) in water (the continuous phase) with stirring. The resulting emulsion is monitored for droplet size, which is in turn controlled by the rate of stirring. The emulsion is then added to water to extract the solvent and to harden the microspheres. The mixture is then filtered and the microspheres are dried under vacuum at room temperature. The desired particle size fraction is then collected by sieving. The microspheres are then suspended in a suitable media for injection such as water.

CONCLUSION

Although the invention has been described above with respect to certain examples, the embodiments depicted in these examples are merely illustrative of various aspects of the invention. In particular, the above Examples are meant to provide a guide to those skilled in the art as to the manufacture of controlled release dosage forms that perform in accordance with the present invention. One skilled in the art will appreciate that these dosage forms have not been tested in-vivo to assure that the requisite effects of the invention are achieved, namely, that the amount of the opioid antagonist included and delivered from the controlled release dosage form during the intended dosing interval is indeed effective to enhance the analgesic potency of the opioid agonist and attenuate the anti-analgesia, hyperalgesia, hyperexcitability, physical dependence and/or tolerance effects of the opioid agonist, or to enhance the analgesic potency of the opioid agonist to the extent that a sub-analgesic amount of the opioid agonist can be delivered from the controlled release dosage form over the dosing interval. However, based on the data contained in U.S. Pat. Nos. 5,512,578; 5,472,943; 5,580,876; and 5,767,125, all to Crain et al. ("the Crain patents"), each of which are hereby incorporated by reference in their entireties, one skilled in the art utilizing the information contained herein would be able to adjust the dosage of the opioid antagonist contained in the dosage form and its release rate without undue experimentation to achieve the requirements of the appended claims. Furthermore, one skilled in the art utilizing the information contained herein will recognize that the dose of opioid agonist included in the examples set forth herein are generally regarded as "analgesic doses" and that the dose of opioid agonist may be adjusted downward to compensate for the enhancement of analgesic potency afforded by the concurrent delivery of the opioid antagonist.

Many obvious modifications may be made to the illustrated examples, and such modifications are considered to be within the scope of the present invention.

What is claimed is:

1. A transdermal delivery system for an opioid analgesic, comprising an opioid agonist and an opioid antagonist contained in a reservoir or matrix and capable of delivery from the system in a controlled manner, such that when the system is applied to the skin of a human patient, the opioid agonist and the opioid antagonist are released at substantially proportionate rates, the opioid agonist is delivered at a mean relative release rate effective to provide analgesia to the patient for at least 3 days, and the opioid antagonist is delivered at a mean relative release rate sufficient to reduce a side effect associated with the opioid agonist, said antagonist selected from the group consisting of naloxone, naltrexone, cyclazocine, levallorphan and pharmaceutically acceptable salts thereof.

2. The transdermal delivery system of claim 1, wherein said opioid antagonist comprises naloxone or a pharmaceutically acceptable salt thereof.

3. The transdermal delivery system of claim 1, wherein said opioid antagonist comprises naltrexone or a pharmaceutically acceptable salt thereof.

4. The transdermal delivery system of claim 1, wherein said opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures thereof and pharmaceutically acceptable salts thereof.

5. The transdermal delivery system of claim 4, wherein said opioid agonist comprises fentanyl or a pharmaceutically acceptable salt thereof.

6. The transdermal delivery system of claim 4, wherein said opioid agonist comprises buprenorphine or a pharmaceutically acceptable salt thereof.

7. The transdermal delivery system of claim 4, wherein said opioid agonist comprises morphine or a pharmaceutically acceptable salt thereof.

8. The transdermal delivery system of claim 4, wherein said opioid agonist comprises hydromorphone or a pharmaceutically acceptable salt thereof.

9. The transdermal delivery system of claim 4, wherein said opioid agonist comprises oxycodone or a pharmaceutically acceptable salt thereof.

10. The transdermal delivery system of claim 1, wherein the opioid antagonist is treated to modify its release rate before it is combined with the opioid agonist, such that when the opioid agonist and the treated antagonist are combined into the transdermal delivery system, the opioid agonist and antagonist are released from the system at substantially proportionate rate.

* * * * *